US011370822B2

(12) United States Patent
Unsworth et al.

(10) Patent No.: US 11,370,822 B2
(45) Date of Patent: Jun. 28, 2022

(54) SELF-ASSEMBLING PEPTIDE FOR ACTIVATING HUMAN MAST CELLS

(71) Applicants: The Governors of the University of Alberta, Edmonton (CA); National Research Council of Canada, Ottawa (CA)

(72) Inventors: Larry D. Unsworth, St. Albert (CA); Lei Lu, Edmonton (CA); Marianna Kulka, Beaumont (CA)

(73) Assignees: The Governors of the University of Alberta, Edmonton (CA); National Research Council of Canada, Ottawa (CA)

( * ) Notice: Subject to any disclaimer, the term of this patent is extended or adjusted under 35 U.S.C. 154(b) by 0 days.

(21) Appl. No.: 16/617,392

(22) PCT Filed: May 25, 2018

(86) PCT No.: PCT/CA2018/050614
§ 371 (c)(1),
(2) Date: Nov. 26, 2019

(87) PCT Pub. No.: WO2018/213934
PCT Pub. Date: Nov. 29, 2018

(65) Prior Publication Data
US 2021/0122799 A1 Apr. 29, 2021

Related U.S. Application Data

(60) Provisional application No. 62/511,729, filed on May 26, 2017.

(51) Int. Cl.
| C07K 14/575 | (2006.01) |
| A61P 37/04 | (2006.01) |
| A61K 9/06 | (2006.01) |
| A61K 38/22 | (2006.01) |
| A61K 45/06 | (2006.01) |
| A61K 47/42 | (2017.01) |
| C07K 7/08 | (2006.01) |

(52) U.S. Cl.
CPC ............ *C07K 14/575* (2013.01); *A61K 9/06* (2013.01); *A61K 38/22* (2013.01); *A61K 45/06* (2013.01); *A61K 47/42* (2013.01); *A61P 37/04* (2018.01); *C07K 7/08* (2013.01); *C07K 2319/735* (2013.01)

(58) Field of Classification Search
CPC .. C07K 14/575; C07K 7/08; C07K 2319/735; A61K 38/22; A61K 45/06; A61K 47/42; A61K 9/06; A61P 37/04
See application file for complete search history.

(56) References Cited

U.S. PATENT DOCUMENTS

| 5,670,483 | A | 9/1997 | Zhang et al. | |
| 6,320,022 | B1 | 11/2001 | Cutitta et al. | |
| 7,179,784 | B2 | 2/2007 | Zhang et al. | |
| 7,449,180 | B2 | 11/2008 | Kisiday et al. | |
| 2003/0171293 | A1* | 9/2003 | Robas | G01N 33/74 514/11.1 |
| 2005/0181973 | A1 | 8/2005 | Genove et al. | |
| 2007/0004630 | A1* | 1/2007 | Cuttitta | A61P 25/00 435/7.8 |
| 2010/0068208 | A1 | 3/2010 | Ogi et al. | |
| 2011/0200560 | A1 | 8/2011 | Zhang | |
| 2014/0066387 | A1 | 3/2014 | Gelain et al. | |
| 2014/0322279 | A1 | 10/2014 | Kumada et al. | |
| 2015/0182596 | A1 | 7/2015 | Lee et al. | |
| 2015/0183828 | A1 | 7/2015 | Genove et al. | |

FOREIGN PATENT DOCUMENTS

CA 2344954 A1 8/2002

OTHER PUBLICATIONS

Hamley et al. Self-Assembly of Peptide Bioconjugates: Selected Recent Research Highlights. Bioconjugate Chemistry, 2017, 28, 731-739. (Year: 2017).*
Ajish et al. Proadrenomedullin N-terminal 20 peptide (PAMP) and its C-terminal 12-residue peptide, PAMP(9-20): Cell selectivity and antimicrobial mechanism. Biochemical and Biophysical Research Communications. Jun. 30, 2020. vol. 527, Issue 3, pp. 744-750. (Year: 2020).*
Galli et al., "Mast Cells in the Development of Adaptive Immune Responses," Nat Immunol. 6(2):135-142 (2005).
Gelain et al., "Designer Self-assembling Peptide Scaffolds for 3-d Tissue Cell Cultures and Regenerative Medicine," Macromolecular Bioscience. 7(5):544-551 (2007).
Gelain et al., "Slow and Sustained Release of Active Cytokines From Self-assembling Peptide Scaffolds," J Control Release. 145(3):231-239 (2010).
Grutzkau et al., "Synthesis, Storage, and Release of Vascular Endothelial Growth Factor/vascular Permeability Factor (Vegf/vpf) by Human Mast Cells: Implications for the Biological Significance of Vegf206," Molecular Biology of the Cell. 9(4): 875-884 (1998).
Gupta et al., "Activation of Human Mast Cells by Retrocyclin and Protegrin Highlight Their Immunomodulatory and Antimicrobial Properties," Oncotarget. 6(30):28573-28587 (2015).
GURISH and AUSTEN, "The Diverse Roles of Mast Cells," J Exp Med. 194(1):F1-F5 (2001).
Harvima et al., "Human Skin Tryptase: Purification, Partial Characterization and Comparison With Human Lung Tryptase," Biochimica et Biophysica Acta (BBA)-Protein Structure and Molecular Enzymology. 957(1):71-80 (1998).

(Continued)

*Primary Examiner* — Marcela M Cordero Garcia
(74) *Attorney, Agent, or Firm* — Clark & Elbing LLP

(57) ABSTRACT

The present disclosure relates to bioactive self-assembling peptides, nanofibers and hydrogels for activating human mast cells. The peptides, nanofibers and hydrogels comprise a self-assembling peptide that mediates self-assembly linked to a MrgX2 agonist peptide; for example, (RADA)4 linked to proadrenomedullin-12 (PAMP-12).

15 Claims, 10 Drawing Sheets

Specification includes a Sequence Listing.

(56) References Cited

OTHER PUBLICATIONS

HAUSER and ZHANG., "Designer Self-assembling Peptide Nanofiber Biological Materials," Chemical Society Reviews. 39(8):2780-2790 (2010).
Heissig et al., "Low-dose Irradiation Promotes Tissue Revascularization Through Vegf Release From Mast Cells and Mmp-9-mediated Progenitor Cell Mobilization," J Exp Med. 202(6):739-750 (2005).
Hirsch et al., "Human Beta-defensin-3 Promotes Wound Healing in Infected Diabetic Wounds," J Gene Med. 11 (3):220-228 (2009).
Horii et al., "Biological Designer Self-Assembling Peptide Nanofiber Scaffolds Significantly Enhance Osteoblast Proliferation, Differentiation and 3-D Migration," Pios One. 2(2):e190 (2007).
Hunt et al., "Immunofluorescent Staining for Mast Cells in Idiopathic Pulmonary Fibrosis: Quantification and Evidence for Extracellular Release of Mast Cell Tryptase," Mayo Clinic Proceedings. 67(10):941-948 (1992).
International Patent Application No. PCT/CA2018/050614, International Preliminary Reporton Patentability dated Nov. 26, 2019.
International Patent Application No. PCT/CA2018/050614, International Search Report and Written Opinion dated Aug. 24, 2018.
Kabiri et al., "Toward a Mechanistic Understanding of Ionic Self-complementary Peptide Selfassembly: Role of Water Molecules and Ions," Biomacromolecules, vol. 14(11), pp. 3943-3950 (2013).
Kamohara et al., "Identification of MrgX2 as a Human G-protein-Coupled Receptor for Proadrenomedullin N-Terminal Peptides," Biochemical and Biophysical Research Communications. 330:1146-1152 (2005).
Kitamura, "Heterogeneity of Mast Cells and Phenotypic Change Between Subpopulations," Annu Rev Immunol. 7:59-76 (1989).
Koutsopoulos et al., "Controlled Release of Functional Proteins Through Designer Selfassembling Peptide Nanofiber Hydrogel Scaffold," Proceedings of the National Academy of Sciences of the United States of America. 106(12):4623-4628 (2009).
Kruger-Krasagakes et al., "Interactions of Immature Human Mast Cells With Extracellular Matrix: Expression of Specific Adhesion Receptors and Their Role in Cell Binding to Matrix Proteins," The Journal of Investigative Dermatology. 106(3):538-543 (1996).
Lam et al., "Ige Alone Stimulates Mast Cell Adhesion to Fibronectin via Pathways Similar to Those Used by Ige Antigen but Distinct From Those Used by Steel Factor," Blood. 102(4):1405-1413 (2003).
Liu et al., "In Vivo Studies on Angiogenic Activity of Two Designer Self-assembling Peptide Scaffold Hydrogels in the Chicken Embryo Chorioallantoic Membrane," Nanoscale. 4(8):2720-2727 (2012).
Mcneil et al. "Identification of a Mast-Cell-Specific Receptor Crucial for Pseudo-allergic Drug Reactions," Nature. 519(7542):237-241 (2015).
Meng et al., "The Effect of a Self-assembling Peptide Nanofiber Scaffold (Peptide) When Used as a Wound Dressing for the Treatment of Deep Second Degree Burns in Rats," Journal of Biomedical Materials Research. Part B, Applied Biomaterials. 89(2):379-391 (2009).
Muramatsu et al., "Chymase Mediates Mast Cell-induced Angiogenesis in Hamster Sponge Granulomas," Eur J Pharmacol. 402(1-2):181-191 (2000).
Nagai et al., "Slow Release of Molecules in Self-assembling Peptide Nanofiber Scaffold," J Control Release. 115(1):18-25 (2006).
Nizet et al., "Innate Antimicrobial Peptide Protects the Skin From Invasive Bacterial Infection," Nature. 414(6862):454-457 (2011).
Norrby et al., "Mast-cell Secretion and Angiogenesis, a Quantitative Study in Rats and Mice," Virchows Arch B Cell Pathol incl Mol Pathol. 57(4):251-256 (1989).
Norrby et al., "Mast-Cell-Mediated Angiogenesis: A Novel Experimental Model Using the Rat Mesentery," Virchows Arch B Cell Pathol Incl Mol Pathol. 52(3):195-206 (1986).
Norrby, "Mast Cells and Angiogenesis," APMIS. 110(5):355-371 (2002).
Pan et al., "Bone Induction by Biomimetic Plga Copolymer Loaded With a Novel Synthetic Rada16-p24 Peptide in Vivo," Mater Sci Eng C Mater Biol Appl. 33(6):3336-3345 (2013).
Qu et al., "Mast Cells Are a Major Source of Basic Fibroblast Growth Factor," Am J Pathol. 147(3):564-573 (1995).
Qu et al., "Synthesis of Basic Fibroblast Growth Factor by Murine Mast Cells. Regulation by Transforming Growth Factor Beta, Tumor Necrosis Factor Alpha, and Stem Cell Factor," International Archives of Allergy and Immunology. 115:47-54 (1998).
RIBATTI and RANIERI., "Tryptase, A Novel Angiogenic Factor Stored in Mast Cell Granules," Exp Cell Res. 332(2):157-162 (2015).
Robas et al., "Mrgx2 is a High Potency Cortistatin Receptor Expressed in Dorsal Root Ganglion," J biol chem. 278(45):44400-44404 (2003).
Rosbottom et al., "TGF-Beta 1 Regulates Adhesion of Mucosal Mast Cell Homologues to Laminin-1 Through Expression of Integrin Alpha 7," J Immunol. 169(10):5689-9565 (2002).
Sadtler et al., "Design, Clinical Translation and Immunological Response of Biomaterials in Regenerative Medicine," Nature Reviews Materials. 1:16040 (2016).
Sadtler et al., "Developing a Pro-regenerative Biomaterial Scaffold Microenvironment Requires T Helper 2 Cells," Science. 352(6283):366-370 (2016).
Saini et al., "Effect of Peptide Concentration on Water Structure, Morphology, and Thermal Stability of Self-Assembling (RADA)4 Peptide Matrices," J Biomater Tissue Eng. 4(11):895-905 (2014).
Scheb-Wetzel et al., "New Insights Into the Antimicrobial Effect of Mast Cells Against Enterococcus Faecalis," Infect Immun. 82(11):4496-4507 (2014).
Schneider et al., "Self-Assembling Peptide Nanofiber Scaffolds Accelerate Wound Healing," PLoS One. 3(1):e1410 (2008) (8 pages).
Kim et al., "Stem cell recruitment and angiogenesis of neuropeptide substance P coupled with self-assembling peptide nanofiber in a mouse hind limb ischemia model," Biomaterials. 34(6):1657-1668 (2013).
Gelain et al., "Designer self-assembling peptide nanofiber scaffolds for adult mouse neural stem cell 3-dimensional cultures," PLoS ONE. 1(1): e119 (2006).
Johnzon et al., "The role of mast cells in bacterial infection, "Am J Pathol. 186(1):4-14 (2016).
Lu et al., "Self-assembling peptide nanoscaffold that activates human mast cells, "ACS Appl Mater Interfaces. 10(7):6107-6117 (2018).
Noli et al., "The mast cell in wound healing,"Vet Dermatol. 12(6):303-313 (2001).
Saini et al., "Evaluation of the hemocompatibility and rapid homeostasis of (RADA)4 peptide-based hydrogels," Acta Biomater. 31:71-79 (2016).
Artuc et al., "Mast Cells and Their Mediators in Cutaneous Wound Healing-Active Participants or Innocent Bystanders?," Experimental Dermatology. 8:1-16 (1999).
Badylak," A Scaffold Immune Microenvironment," Science. 352(6283):298 (2016).
Blatman et al., "Expression of Mast Cell-associated Genes is Upregulated in Adult Eosinophilic Esophagitis and Responds to Steroid or Dietary Therapy," J Allergy Clin Immunol. 127(5):1307-8.e3 (2011).
Butrus et al., "The Level of Tryptase in Human Tears. An Indicator of Activation of Conjunctival Mast Cells," Ophthalmology. 97(12):1678-1683 (1990).
Calderhead et al., "One Mechanism Behind Led Phototherapy for Wound Healing and Skin Rejuvenation: Key Role of the Mast Cell," Laser Therapy. 17(3):141-148 (2008).
Christy et al., "Mast Cell Activation and Neutrophil Recruitment Promotes Early and Robust Inflammation in the Meninges in Eae," J Autoimmun. 42:50-61 (2013).
DASTYCH and METCALFE, "Stem Cell Factor Induces Mast Cell Adhesion to Fibronectin," J Immunol. 152(1):213-219 (1994).
Deng et al., "Impact of Actin Rearrangement and Degranulation on the Membrane Structure of Primary Mast Cells: A Combined

(56) References Cited

OTHER PUBLICATIONS

Atomic Force and Laser Scanning Confocal Microscopy Investigation," Biophysical Journal. 96(4):1629-1639 (2009).
Douaiher et al., "Development of Mast Cells and Importance of Their Tryptase and Chymase Serine Proteases in Inflammation and Wound Healing," Adv Immunol. 122:211-252 (2014).
Draber et al., "Cytoskeleton in Mast Cell Signaling," Front Immunol. 3:130 (2012).
DUPLANTIER and Van Hoek., "The Human Cathelicidin Antimicrobial Peptide LI-37 as a Potential Treatment for Polymicrobial Infected Wounds," Front Immunol. 4:143 (2013).
Ellis-Behnke et al., "Nano Neuro Knitting: Peptide Nanofiber Scaffold for Brain Repair and Axon Regeneration With Functional Return of Vision," Proceedings of the National Academy of Sciences of the United States of America. 103(13):5054-5059 (2006).
Feger et al., "The Role of Mast Cells in Host Defense and Their Subversion by Bacterial Pathogens," Trends Immunol. 23(3):151-158 (2002).
Gailit et al., "The Differentiation and Function of Myofibroblasts is Regulated by Mast Cell Mediators," J Invest Dermatol. 117(5):1113-1119 (2011).
Schwartz et al., "Tryptase Levels as an Indicator of Mast-cell Activation in Systemic Anaphylaxis and Mastocytosis," N Engl J Med. 316(26):1622-1626 (1987).
Shiota et al., "Pathophysiological Role of Skin Mast Cells in Wound Healing After Scald Injury: Study With Mast Cell-deficient W/w(V) Mice," Int arch allergy Immunol. 151(1):80-88 (2010).
Subramanian et al., "Beta-Defensins Activate Human Mast Cells via Mas-related Gene X2," J Immunol. 191(1):345-352 (2013) (9 pages).
Subramanian et al., "Mas-related Gene X2 (Mrgx2) is a Novel G Protein-coupled Receptor for the Antimicrobial Peptide LI-37 in Human Mast Cells: Resistance to Receptor Phosphorylation, Desensitization, and Internalization," J Biol Chern. 286(52):44739-44749 (2011) (12 pages).
Tatemoto et al., "Immunoglobulin E-Independent Activation of Mast Cell is Mediated by Mrg Receptors," Biochem Biophys Res Commun. 349(4):1322-1328 (2006).
Tellechea et al., "Mast Cells Regulate Wound Healing in Diabetes," Diabetes. 65(7):2006-2019 (2016) (45 pages).
Thompson et al., "Regulation of Adhesion of Mouse Bone Marrow-derived Mast Cells to Laminin," J Immunol. 145(10):3425-3431 (1990).
Trautmann et al., "Human Mast Cells Augment Fibroblast Proliferation by Heterotypic Cell-cell Adhesion and Action of II-4," J Immunol. 160(10):5053-5057 (1998) (6 pages).
Velasquez et al., "Alpha Tryptase Allele of Tryptase 1 (Tpsabl) Gene Associated With Dengue Hemorrhagic Fever (Dhf) and Dengue Shock Syndrome (Dss) in Vietnam and Philippines," Hum Immunol. 76(5):318-223 (2015).
Vigneswaran et al., "Peptide Biomaterials Raising Adaptive Immune Responses in Wound Healing Contexts," J Biomed Mater Res A. 104(8):1853-1862 (2016).
Vliagoftis, "Thrombin Induces Mast Cell Adhesion to Fibronectin: Evidence for Involvement of Protease-activated Receptor-1," J Immunol. 169(8):4551-4558 (2002) (9 pages).
Walls et al., "Immunohistochemical Identification of Mast Cells in Formaldehyde-fixed Tissue Using Monoclonal Antibodies Specific for Tryptase," J Pathol. 162(2):119-126 (1990).
Wang et al., "Designer Functionalized Self-assembling Peptide Nanofiber Scaffolds for Growth, Migration, and Tubulogenesis of Human Umbilical Vein Endothelial Cells," Soft Matter. 4(12):2388-2395 (2008).
Wang et al., "Human Hypertrophic Scar-like Nude Mouse Model: Characterization of the Molecular and Cellular Biology of the Scar Process," Wound Repair Regen. 19(2):274-285 (2011).
WERNERSSON and PEJLER, "Mast Cell Secretory Granules: Armed for Battle," Nat Rev Immunol. 14(7):478-494 (2014).
Wu et al., "The Origin, Expression, Function and Future Research Focus of a G Protein-Coupled Receptor, Mas-Related Gene X2 (MrgX2)," Prog Histochem Cytochem. 50 (1-2):11-17 (2015).
WULFF and WILGUS, "Mast Cell Activity in the Healing Wound: More Than Meets the Eye?" Exp Dermatol. 22(8):507-510 (2013).
Yokoi et al., "Dynamic Reassembly of Peptide Rada16 Nanofiber Scaffold," Proc Natl Acad Sci U Sa. 102(24):8414-8419 (2005).
Zanetti, "Cathelicidins, Multifunctional Peptides of the Innate Immunity," J Leukoc Biol. 75(1):39-48 (2004).
Zhang et al., "Designer Self-assembling Peptide Nanofiber Scaffolds for 3d Tissue Cell Cultures," Semin Cancer Biol. 15(5):413-420 (2005).
ZHANG. "Emerging Biological Materials Through Molecular Self-assembly," Biotechnology Advances, 20(5-6):321-339 (2002).
Zhang, "Fabrication of Novel Biomaterials Through Molecular Self-Assembly," Nat Biotechnol. 21(10):1171-1178(2003).
Zou et al., "Biocompatibility and Bioactivity of Designer Self-assembling Nanofiber Scaffold Containing FGL Motif for Rat Dorsal Root Ganglion Neurons," J Biomed Mat Res A. 95(4):1125-1131 (2010).
Zou et al., "Biocompatibility of Functionalized Designer Self-assembling Nanofiber Scaffolds Containing Frm Motif for Neural Stem Cells," J Biomed Mat Res A. 102(5):1286-1293 (2014).

\* cited by examiner (RADA)₄: AC-RADARADARADARADA-CONH₂;

(SEQ ID NO: 1)

(RADA)₄-GG-(PAMP-12): AC-RADARADARADARADA-GG-FRKKWNKWALSR-CONH₂

(SEQ ID NO: 2)

(SEQ ID NO: 2)

a)

b)

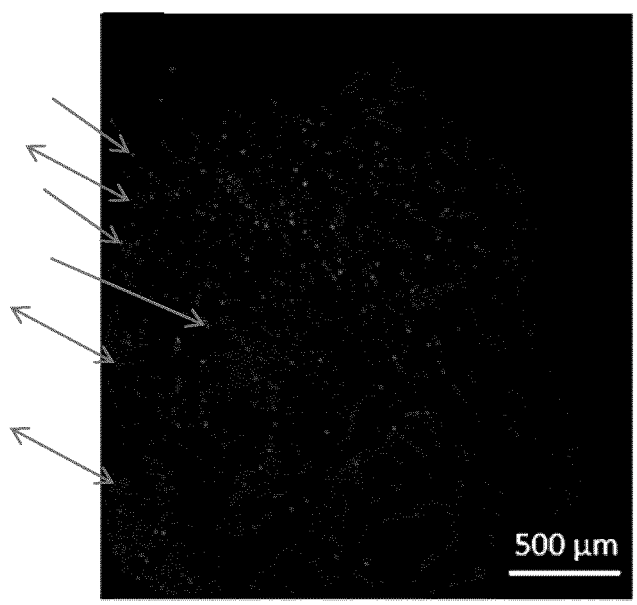
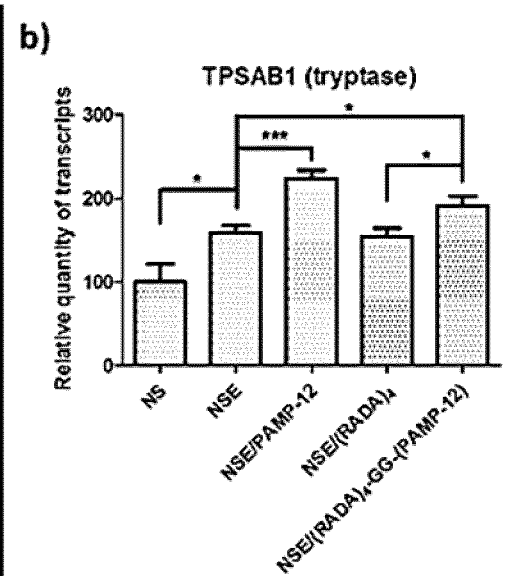
FIG. 9A
FIG. 9B

SEQUENCE LISTING

```
<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: peptide

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 30
<212> TYPE: PRT
<213> ORGANISM: Artificial Sequence
<220> FEATURE:
<223> OTHER INFORMATION: peptide
```

```
<400> SEQUENCE: 2

Arg Ala Asp Ala Arg Ala Asp Ala Arg Ala Asp Ala Arg Ala Asp Ala
1               5                   10                  15

Gly Gly Phe Arg Lys Lys Trp Asn Lys Trp Ala Leu Ser Arg
            20                  25                  30

<210> SEQ ID NO 3
<211> LENGTH: 12
<212> TYPE: PRT
<213> ORGANISM: Artificial Sequence
<220> FEATURE:
<223> OTHER INFORMATION: peptide

<400> SEQUENCE: 3

Phe Arg Lys Lys Trp Asn Lys Trp Ala Leu Ser Arg
1               5                   10
```

SELF-ASSEMBLING PEPTIDE FOR ACTIVATING HUMAN MAST CELLS

CROSS REFERENCE TO RELATED APPLICATION

This application claims priority to U.S. 62/511,729, filed May 26, 2017, the entire contents of which is hereby incorporated by reference.

FIELD

The present disclosure relates generally to self-assembling peptides for activating human mast cells.

BACKGROUND

Traditionally, mast cells are best known for their important role in allergic inflammatory responses, however, mast cells also participate in protective actions such as wound healing, angiogenesis and host defense against pathogens and animal venoms [1-5]. Mature mast cells are distributed widely in connective tissues that interface with the external environment throughout the body: skin, digestive tract, mucosa of lung and airways, etc. [6, 7]. These cells contain a number of secretory granules, which are filled with a large amount of pre-formed and pre-activated compounds like histamine, heparin and serine proteases, cytokines and growth factors [1, 8]. Upon stimulation, mast cell degranulation occurs and leads to the rapid release of pre-stored and neo-synthesized mediators. Therefore, mast cells can be considered as the first responders that play a critical role in both host defense and tissue repair.

SUMMARY

In one aspect there is described a bioactive self-assembling peptide, comprising: a first peptide comprising a self-assembling peptide that mediates self-assembly; and a second peptide comprising a MrgX2 agonist.

In one example, the bioactive self-assembling peptide of claim 1, further comprising a linker positioned between said first peptide and said second peptide.

In one aspect there is described a bioactive self-assembling peptide, comprising: a first peptide comprising a self-assembling peptide that mediates self-assembly; and a second peptide comprising a MrgX2 agonist; and a linker positioned between said first peptide and said second peptide.

In one example, the bioactive self-assembling peptide of any preceding claim, wherein said linker comprises a peptide, preferably at least two peptides.

In one example, the bioactive self-assembling peptide of any preceding claim, wherein said linker comprises the amino acid sequence Gly-Gly.

In one example, the bioactive self-assembling peptide of any preceding claim, wherein said first peptide comprises the peptide (RADA)4 (SEQ ID NO: 1).

In one example, the bioactive self-assembling peptide of any preceding claim, wherein said second peptide comprises PAMP12.

In one aspect there is described a nanofiber comprising a bioactive self-assembling peptide according to any preceding claim.

In one aspect there is described a hydrogel comprising a bioactive self-assembling peptide according to any one of claims 1 to 8, and a liquid.

In one example, the hydrogel of claim 9, comprising at least about 20% (w/w) said bioactive self-assembling peptide.

In one aspect there is described a hydrogel comprising a bioactive self-assembling peptide according to any one of claims 1 to 8, a self-assembling peptide, and a liquid.

In one example, the hydrogel of claim 11, comprising at least about 20% (w/w) said bioactive self-assembling peptide.

In one aspect there is described a use of a bioactive self-assembling peptide according to any one of claims 1-8, for activation of a mast cell in a subject.

In one aspect there is described a use of a bioactive self-assembling peptide according to any one of claims 1-8, for the treatment of a bacterial infection in a subject.

In one aspect there is described a use of a bioactive self-assembling peptide according to any one of claims 1-8, for the treatment of a wound in a subject.

In one aspect there is described a use of a nanofiber of claim 9, for activation of a mast cell in a subject.

In one aspect there is described a use of a nanofiber of claim 9, for the treatment of a bacterial infection in a subject.

In one aspect there is described a use of a nanofiber of claim 9, for the treatment of a wound a subject.

In one aspect there is described a use of a hydrogel of any one of claims 10 to 13, for activation of a mast cell in a subject.

In one aspect there is described a use of a hydrogel of any one of claims 10 to 13, for the treatment of a bacterial infection in a subject.

In one aspect there is described a use of a hydrogel of any one of claims 10 to 13, for the treatment of a wound in a subject.

In one aspect there is described a use of a bioactive self-assembling peptide according to any one of claims 1-8, in the manufacture of a medicament for activation of a mast cell in a subject.

In one aspect there is described a use of a bioactive self-assembling peptide according to any one of claims 1-8, in the manufacture of a medicament for the treatment of a bacterial infection in a subject.

In one aspect there is described a use of a bioactive self-assembling peptide according to any one of claims 1-8, in the manufacture of a medicament for the treatment of a wound in a subject.

In one example, the use of the bioactive self-assembling peptide further comprises use of an antibiotic.

In one aspect there is described a use of a nanofiber, in the manufacture of a medicament for activation of a mast cell in a subject.

In one aspect there is described a use of a nanofiber, in the manufacture of a medicament for the treatment of a bacterial infection in a subject.

In one aspect there is described a use of a nanofiber, in the manufacture of a medicament for the treatment of a wound in a subject.

In one aspect there is described a use of a hydrogel in the manufacture of a medicament for activation of a mast cell in a subject.

In one aspect there is described a use of a hydrogel in the manufacture of a medicament for the treatment of a bacterial infection in a subject.

In one aspect there is described a use of a hydrogel in the manufacture of a medicament for the treatment of a wound a subject.

In one example, the use of the hydrogel further comprises use of an antibiotic in the manufacture of a medicament for the treatment of a bacterial infection.

In one example of the use, wherein said subject is a human.

In one aspect there is described a method of treating a bacterial infection, comprising: administering a bioactive self-assembling peptide to a subject in need thereof.

In one aspect there is described a method of treating a bacterial infection, comprising: administering a nanofiber to a subject in the need thereof.

In one aspect there is described a method of treating a bacterial infection, comprising: administering a hydrogel to a subject in the need thereof.

In one example, the method further comprises administering an antibiotic.

In one example of the method, said subject is a human.

In one aspect there is described a method of treating a wound in a subject, comprising: administering a bioactive self-assembling peptide to a subject in the need thereof.

In one aspect there is described a method of treating a wound in a subject, comprising: administering a nanofiber a subject in the need thereof.

In one aspect there is described a method of treating a wound in a subject, comprising: administering a hydrogel to a subject in need thereof.

In one example, the method further comprises administering an antibiotic.

In one example of the method, said subject is a human.

In one aspect there is described a kit comprising: a bioactive self-assembling peptide, a container, and optionally instructions for the use thereof.

In one aspect there is described a kit comprising: a nanofiber, a container, and optionally instructions for the use thereof.

In one aspect there is described a kit comprising: a hydrogel a container, and optionally instructions for the use thereof.

In one example, the kit further comprises an antibiotic.

BRIEF DESCRIPTION OF THE FIGURES

Embodiments of the present disclosure will now be described, by way of example only, with reference to the attached Figs.

FIG. 9 a) Immunofluorescent staining of human skin. Nuclei (blue—some examples shown with leader line with double arrows), mast cell tryptase (red—some examples shown with leader line with single arrow). b) ddPCR analysis of TPSAB1 (tryptase) mRNA for human skin tissue treated with hydrogel matrices or PAMP-12 for 4 h. Expression was normalized with the expression of ACTB. NS: normal skin, NSE: normal skin without epidermis, NSE/PAMP-12: NSE with 10 μM PAMP-12, NSE/(RADA)4: NSE with pure (RADA)4 hydrogel matrix, NSE/$(RADA)_4$-GG-(PAMP-12): NSE with hydrogel matrix contain 20% w/w $(RADA)_4$-GG-(PAMP-12). Data represent mean±1 SEM, for n≥3 repeats.

DETAILED DESCRIPTION

Figures 1A, 1B:
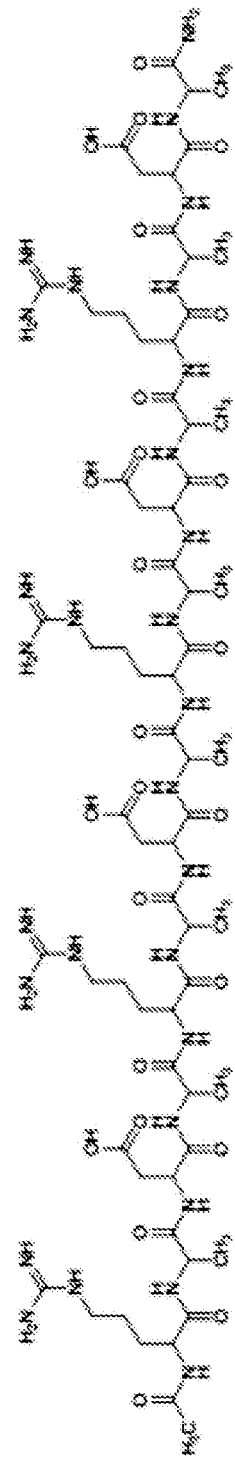
FIG. 1 depicts the chemical structure of self-assembling peptides, (A) (RADA)4 (SEQ ID NO: 1), (B&C) (RADA)4GG(PAMP12) (SEQ ID NO:2).

Generally, the present disclosure provides compounds, compositions, methods, and uses, for mast cell activation in a subject.

In one example, the compounds, compositions, methods, and uses, for mast cell activation are used in the treatment of a bacterial infection in a subject.

There term "subject" as used herein refers to an animal. Is some examples, the animal is a mammal. Non-limiting examples of mammals include a human; a non-human primate; a companion animal such as a mouse, rat, dog, cat, hamster, guinea pig, rabbit; livestock such a cow, sheep, horse, prig, chicken; and the like. A subject may also be referred to as a patient.

In some examples, there is described a bioactive self-assembling peptide, comprising: a first peptide comprising a self-assembling peptide that mediates self-assembly; and a second peptide comprising a MrgX2 agonist.

In one example, the bioactive self-assembling peptide further comprises a linker positioned between said first peptide and said second peptide.

In some examples, there is described a bioactive self-assembling peptide, comprising: a first peptide comprising a self-assembling peptide that mediates self-assembly; and a second peptide comprising a MrgX2 agonist; and a linker positioned between said first peptide and said second peptide.

In some examples bioactive the self-assembling peptide is for use in mast cell activation in a subject.

In one example, the bioactive self-assembling peptide is for use in the treatment of a bacterial infection in a subject.

In one example, the bioactive self-assembling peptide forms nanofibers.

In one example, the nanofiber(s) produced from the bioactive self-assembling peptides is for use in mast cell activation in a subject.

In one example, the nanofiber(s) produced from the bioactive self-assembling peptides are for use in the treatment of a bacterial infection in a subject.

In one example, the bioactive self-assembling peptide(s) as described herein a used to prepare a hydrogel for mast cell activation.

In one example, the bioactive self-assembling peptide(s) as described herein a used to prepare a hydrogel for mast cell activation, for use in the treatment of a bacterial infection in a subject.

In one example, the bioactive self-assembling peptide is for the preparation of a medicament for use in the treatment of a bacterial infection in a subject.

The terms "peptide", "polypeptide," and "protein" are used interchangeably to refer to a polymer of amino acid residues. The terms also apply to amino acid polymers in which one or more amino acid residue is an analog or mimetic of a corresponding naturally occurring amino acid, as well as to naturally occurring amino acid polymers. The terms encompass any peptide (including cyclic peptides) or protein comprising two or more amino acids joined to each other by peptide bonds or modified peptide bonds. "Polypeptide" refers to both short chains, commonly referred to as peptides, oligopeptides or oligomers, and to longer chains, generally referred to as proteins.

A peptide may contain amino acids other than the 20 gene-encoded amino acids. When amino acids are not designated as either D- or L-amino acids, the amino acid is either an L-amino acid or could be either a D- or L-amino acid, unless the context requires a particular isomer Peptides can be produced using methods known in the art, e.g., by purifying the peptide sequence from a naturally occurring protein or peptide. Purification can be performed along with a cleavage or degradation (either enzymatic or non-enzymatic) to produce the desired peptide using methods known in the art.

Alternatively, products can be biochemically synthesized using, e.g., solid phase synthesis, partial solid phase synthesis methods, fragment condensation, classical solution synthesis.

Peptides may also be prepared, for example, by isolation from genetically engineered host cells comprising expression systems. For example, peptides described herein may be produced by expressing in a cell (e.g., a yeast, bacterial, mammalian, or insect cell) a vector containing a polynucleotide that encodes a peptide under condition in which the peptide is expressed. Means for preparing such peptides are well understood in the art.

Peptides of the present disclosure also include variants of the aforementioned peptides, including all allelic forms and splice variants. Such peptides vary from the reference peptide by insertions, deletions, and substitutions that may be conservative or non-conservative, or any combination thereof.

The term "self-assembling" refers to the capability of one or more molecules in a compound to spontaneously assemble, or organize, to form a high ordered structure. For example, a plurality of molecules of a compound in which a disordered system forms a more organized structure or pattern as a consequence of specific, local interactions among the molecules themselves, without external direction. In a specific example, a "self-assembling peptide" refers to the capacity of amino acid residues in a peptide to spontaneously assemble, of organize, to form a higher order structure. In one example, the higher order structure is a nanofiber. In one example, the higher order structure is a hydrogel.

In a specific example, the first peptide comprises a (RADA)$_4$ peptide (RADARADARADARADA) (SEQ ID NO: 1).

In the case of (RADA)$_4$ (SEQ ID NO: 1), while not wishing to be bound by theory, it is thought alternating hydrophobic and hydrophilic amino acids form well-ordered β-sheet nanofibers through self-assembly.

The term "linker" as used herein refers to an agent or molecule that connects said first peptide and said second peptide. In one example, the linker covalently connects said first peptide to said second peptide. In another example, the linked non-covalently connects said first peptide to said second peptide.

In one example, the linker refers to an amino acid sequence that connects or links the first peptide and second peptide.

In one example, the linker is one or more amino acid residues positioned between said first peptide and said second peptide. In one example, the linker is at least one amino acid. In one example, the linker is at least two amino acids. In one example, the linker is at least three amino acids. In one example, the linker is four or more amino acids. In one example, the amino acids within the liker may be the same or different.

In one example, the linker is GlyGly (GG).

The term "MrgX2 agonist" as used herein refers to an agonist of the MrgX2 receptor.

The term "agonist" or "receptor agonist" refers to a type of ligand or drug or compound that binds and alters the activity of a receptor. The ability to alter the activity of a receptor, also known as the agonist's efficacy, is a property that distinguishes it from antagonists, a type of receptor ligand which also binds a receptor but which does not alter the activity of the receptor. The efficacy of an agonist may be positive, causing an increase in the receptors activity or negative causing a decrease in the receptors activity.

In a specific example, the MrgX2 agonist comprises a PAMP12 peptide (FRKKWNKWALSR) (SEQ ID NO: 3).

In a specific example, the bioactive self-assembling peptide is (RADA)$_4$-GG-(PAMP-12) (SEQ ID NO: 2).

In one example, the MrgX2 agonist is useful for activation of mast cells.

The term "mast cell" refers to a granulocyte that contains granules. In some embodiments, the term "mast cell" refers to a mastocyte. In some embodiments, the term "mast cell" refers to a labrocyte. In some embodiments, the term "mast cell" refers to a leukocyte. In some embodiments, the term "mast cell" refers to an inactivated mast cell. In some embodiments the term "mast cell" refers to an activated mast cell. In some embodiments, the term "mast cell" refers to a mast cell residing in the bone marrow, in the systemic circulatory system, and/or in organ tissues. In some embodiments, the organ tissue is the lung, the skin, the heart, the brain, the eye, the gastrointestinal tract, the thymus, the spleen, the ear, the nose or combinations thereof.

The term "degranulation" of mast cells refers to a cellular process that releases antimicrobial and/or cytotoxic molecules from secretory vesicles (also referred to as granules) found in mast cells.

In one example, the degranulation activity increased proportionally with the increase in (RADA)$_4$-GG-(PAMP-12) (SEQ ID NO: 2) from 2.5 to 20% w/w, and the degranulation activity at 20% and 40% w/w of (RADA)$_4$-(PAMP-12) (SEQ ID NO: 2).

Although best known for their role in allergy and anaphylaxis, mast cells play an important protective role as well, being intimately involved in defense against pathogens, such as bacteria.

Accordingly, activation of mast cells may be used in the treatment of bacterial infection.

In some examples, mast cells may be used in the treatment of a wound.

Accordingly, activation may be used in the treatment of wounds in a subject.

As used herein, "wound" refers broadly to injuries to an organ or tissue of an subject that typically involves division of tissue or rupture of a membrane (e.g., skin), due to external violence, a mechanical agency, or infectious disease.

A wound can be an epithelial, endothelial, connective tissue, ocular, or any other kind of wound in which the strength and/or integrity of a tissue has been reduced, e.g. trauma has caused damage to the tissue.

The term "wound" encompasses injuries including, but not limited to, lacerations, abrasions, avulsions, cuts, burns, velocity wounds (e.g., gunshot wounds), penetration wounds, puncture wounds, contusions, diabetic wounds, hematomas, tearing wounds, and/or crushing injuries.

In one example, the term "wound" refers to an injury to the skin and subcutaneous tissue initiated in any one of a variety of ways (e.g., pressure sores from extended bed rest, wounds induced by trauma, cuts, ulcers, burns and the like) and with varying characteristics.

As used herein, the term "wound healing" refers to a process by which the body of a wounded subject initiates repair of a tissue at the wound site (e.g., skin).

Wound healing can be measured by assessing such parameters as contraction, area of the wound, percent closure, percent closure rate, and/or infiltration of blood vessels as known to those of skill in the art.

In some examples, the self-assembling peptides, nanofibers, and hydrogels, are used to treat a wound in a subject.

In some examples, the self-assembling peptides, nanofibers, and hydrogels, are used to promote wound healing in a subject.

The terms "treat" and "treatment" refer to both therapeutic treatment and prophylactic or preventative measures, wherein the object is to prevent or decrease an undesired physiological change or disorder, such as a bacterial infection. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In one example treatment is in vitro treatment. In one example, treatment is in vivo treatment.

As used herein, the term "infection" refers to any state in at least one cell, for example a cell of a subject, is infected by an infectious agent, such as a bacterium or bacteria As referred to herein, the term "bacteria" refers to members of a large domain of prokaryotic microorganisms.

In some examples, the bacteria comprise gram-negative bacteria.

In some examples, the bacteria comprise gram-positive bacteria.

Bacteria may be antibiotic-sensitive or an antibiotic-resistant.

As used herein, the term "bacteria" (and derivatives thereof, such as "microbial infection") includes, but is not limited to, references to organisms (or infections due to organisms) of the following classes and specific types: Gram-positive cocci, such as Staphylococci (e.g. Staph, aureus, Staph, epidermidis, Staph. saprophyticus, Staph, auricuiaris, Staph, capitis capitis, Staph, c. ureolyticus, Staph, caprae, Staph, cohnii cohnii, Staph, c. ureaiyticus, Staph, equorum, Staph, galiinarum, Staph. haemolyticus, Staph, hominis hominis, Staph, h, novobiosepticius, Staph, hyicus, Staph. intermedius, Staph, iugdunensis, Staph, pasteuri, Staph, saccharolyticus, Staph, schleiferi schleiferi, Staph, s. coagulans, Staph, sciuri, Staph, simuians, Staph, warneri and Staph. xylosus); Streptococci (e.g. beta-haemoiytic, pyogenic streptococci (such as Strept, agaiactiae, Strept. canis, Strept. dysgalactiae dysgalactiae, Strept. dysgaiactiae equisimiiis, Strept. equi equi, Strept. equi zooepidemicus, Strept. iniae, Strept. porcinus and Strept. pyogenes), microaerophilic, pyogenic streptococci (*Streptococcus* "milled", such as Strept. anginosus, Strept. consteiiatus consteiiatus, Strept. consteiiatus pharyngidis and Strept. intermedius), oral streptococci of the "mitis" (alpha-haemolytic—*Streptococcus* "viridans", such as Strept. mitis, Strept. oralis, Strept. sanguinis, Strept. cristatus, Strept. gordonii and Strept. parasanguinis), "salivarius" (non-haemolytic, such as Strept. saiivarius and Strept. vestibularis) and "mutans" (tooth—surface streptococci, such as Strept. criceti, Strept. mutans, Strept. ratti and Strept, sobrinus) groups, Strept. acidominimus, Strept, bovis, Strept, faecalis, Strept. equinus, Strept. *pneumoniae* and Strept. suis, or Streptococci alternatively classified as Group A, B, C, D, E, G, L, P, U or V *Streptococcus*); Gram-negative cocci, such as *Neisseria gonorrhoeae, Neisseria meningitidis, Neisseria cinerea, Neisseria eiongata, Neisseria fiavescens, Neisseria iactamica, Neisseria mucosa, Neisseria sicca, Neisseria* subfiava and *Neisseria* weavers; Bacillaceae, such as *Baciiius anthracis, Baciius subtilis, Baciiius thuringiensis, Bacillus* stearothermophiius and *Bacillus cereus*; Enterobacteriaceae, such as *Escherichia coli, Enterobacter* (e.g. *Enterobacter aerogenes, Enterobacter* aggiomerans and *Enterobacter cloacae*), *Citrobacter* (such as Citrob. *freundii* and Citrob. divernis), Hafnia (e.g. Hafnia *alvei*), *Erwinia* (e.g. *Erwinia* persicinus), Morganeila *morganii, Salmonella* (*Salmonella enterica* and *Salmonella typhi*), *Shigella* (e.g. *Shigella dysenteriae, Shigella fiexneri, Shigella boydii* and *Shigella sonnei*), *Klebsiella* (e.g. Klebs. *pneumoniae*, Klebs. *oxytoca*, Kiebs. ornithoiytica, Kiebs. pianticola, Kiebs. ozaenae, Klebs. *terrigena*, Klebs. granuiomatis (*Calymmatobacterium granulomatis*) and Kiebs. rhinoscleromatis), *Proteus* (e.g. Pr. *mirabilis*, Pr. *rettgeri* and Pr. vulgaris), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*); Enterococci (e.g. *Enterococcus avium, Enterococcus casseiifiavus, Enterococcus cecorum, Enterococcus dispar, Enterococcus durans, Enterococcus faecaiis, Enterococcus faecium, Enterococcus fiavescens, Enterococcus gailinarum, Enterococcus hirae, Enterococcus maiodo-* ratus, *Enterococcus mundtii, Enterococcus pseudoavium, Enterococcus* raffinosus and *Enterococcus solitarius*); *Helicobacter* (e.g. *Helicobacter pylori, Helicobacter cinaedi* and *Helicobacter fennelliae*); *Acinetobacter* (e.g. *A. baumanii, A. calcoaceticus, A. haemolyticus, A. johnsonii, A. junii, A. Iwoffi* and *A. radioresistens*); *Pseudomonas* (e.g. *Ps. aeruginosa, Ps. maltophiiia {Stenotrophomonas maltophiiia), Ps. alcaiigenes, Ps. chiororaphis, Ps. fluorescens, Ps. iuteola. Ps. mendocina, Ps. monteilii, Ps. oryzihabitans, Ps. pertocinogena, Ps. pseudalcaligenes, Ps. putida* and *Ps. stutzeri*); *Bacteroides fragilis; Peptococcus* (e.g. *Peptococcus niger*); *Peptostreptococcus; Clostridium* (e.g. *C. perfringens, C. difficile, C. botuiinum, C. tetani, C. absonum, C. argentinense, C. baratii, C. bifermentans, C. beijerinckii,* C. butyricu, *C. cadaveris, C. carnis, C. celatum,* C. ciostridioforme, C. cochiearium, C. cocieatum, *C. fallax, C. ghonii, C. glycolicum, C. haemolyticum, C. hastiforme, C. histolyticum, C. indoiis, C. innocuum, C. irregulare, C. leptum, C. limosum, C. malenominatum, C. novyi, C. oroticum, C. paraputrificum, C. pi!iforme, C. puirefasciens, C. ramosum, C, septicum, C. sordelii, C. sphenoides, C. sporogenes, C. subterminale, C. symbiosum* and *C. tertium*); *Mycoplasma* (e.g. *M. pneumoniae, M. hominis, M. genitaiium* and *M. ureaiyticum*); *Mycobacteria* (e.g. *Mycobacterium tuberculosis, Mycobacterium avium, Mycobacterium fortuitum, Mycobacterium marinum, Mycobacterium kansasii, Mycobacterium cheionae, Mycobacterium abscessus, Mycobacterium leprae, Mycobacterium smegmitis, Mycobacterium africanum, Mycobacterium aivei, Mycobacterium asiaticum, Mycobacterium aurum, Mycobacterium bohemicum, Mycobacterium bovis, Mycobacterium branderi, Mycobacterium brumae, Mycobacterium ceiatum, Mycobacterium chubense, Mycobacterium confiuentis, Mycobacterium conspicuum, Mycobacterium cookii, Mycobacterium fiavescens, Mycobacterium gadium, Mycobacterium gastri, Mycobacterium genavense, Mycobacterium gordonae, Mycobacterium goodii, Mycobacterium haemophiium, Mycobacterium hassicum, Mycobacterium intraceiluiare, Mycobacterium interjectum, Mycobacterium heideiberense, Mycobacterium ientifiavum, Mycobacterium maimoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabiie, Mycobacterium triplex, Mycobacterium triviale, Mycobacterium tusciae, Mycobacterium ulcerans, Mycobacterium vaccae, Mycobacterium wolinskyi* and *Mycobacterium xenopi*); *Haemophilus* (e.g. *Haemophilus influenzae, Haemophilus ducreyi, Haemophilus aegyptius, Haemophilus parainfiuenzae, Haemophilus haemolyticus* and *Haemophilus parahaemoiyticus*); *Actinobacillus* (e.g. *Actinobacillus actinomycetemcomitans, Actinobacilius equuii, Actinobacillus hominis, Actinobacillus iignieresii, Actinobacillus suis* and *Actinobacilius ureae*); *Actinomyces* (e.g. *Actinomyces israelii*); *Brucella* (e.g. *Brucella abortus, Brucella canis, Brucella melintensis* and *Brucella suis*); *Campylobacter* (e.g. *Campylobacter jejuni, Campylobacter coil, Campylobacter iari* and *Campylobacter fetus*); *Listeria monocytogenes; Vibrio* (e.g. *Vibrio choierae* and *Vibrio parahaemoiyticus, Vibrio alginolyticus, Vibrio carchariae, Vibrio fluvialis, Vibrio furnissii, Vibrio hoilisae, Vibrio metschnikovii, Vibrio mimicus* and *Vibrio vulnificus*); *Erysipelothrix rhusopathiae*; Corynebacteriaceae (e.g. *Corynebacieriurn diphtheriae, Corynebacterium jeikeum* and *Corynebacterium ureaiyticum*); Spirochaeiaceae, such as *Borrelia* (e.g. *Borrelia recurrentis, Borrelia burgdorferi, Borrelia afzeiii, Borrelia andersonii, Borrelia bissettii, Borrelia garinii, Borrelia japonica, Borrelia iusitaniae, Borrelia tanukii, Borrelia turdi, Borrelia vaiaisiana, Borrelia caucasica, Borrelia crocidurae, Borrelia duttoni, Borrelia graingen, Borrelia hermsii, Borrelia hispanica, Borrelia iatyschewii, Borrelia mazzottii, Borrelia parkeri, Borrelia persica, Borrelia turicatae* and *Borrelia venezueiensis*) and *Treponema* (*Treponema pallidum* ssp. *pallidum, Treponema pallidum* ssp. *endemicum, Treponema pallidum* ssp. *pertenue* and *Treponema carateum*); *Pasteurelia* (e.g. *Pasteurelia aerogenes, Pasteureiia bettyae, Pasteurelia canis, Pasteurelia dagmatis, Pasteureiia gallinarum, Pasteureiia haemolytica, Pasteureiia muitocida multocida, Pasteureiia muitocida gaiiicida, Pasteureiia multocida septica, Pasteureiia pneumotropica* and *Pasteureiia stomatis*); *Bordeteila* (e.g. *Bordeteila bronchiseptica, Bordeteila hinzii, Bordetelia hoimseii, Bordeteila parapertussis, Bordeteila pertussis* and *Bordeteila trematum*); Nocardiaceae, such as *Nocardia* (e.g. *Nocardia asteroides* and *Nocardia brasiiiensis*); *Rickettsia* (e.g. *Ricksettsii* or *Coxieiia burnetii*); *Legionella* (e.g. *Legionalia anisa, Legionella birminghamensis, Legionella bozemanii, Legionella cincinnatiensis, Legionella dumoffii, Legionella feeieii, Legionella gormanii, Legionella hackeliae, Legionella israelensis, Legionella jordanis, Legionalia lansingensis, Legionalia longbeachae, Legionalia maceachernii, Legionalia micdadei, Legionalia oakridgensis, Legionalia pneumophila, Legionalia sainthelensi, Legionalia tucsonensis* and *Legionella wadsworthii*); *Moraxelia catarrhal is; Cyclospora cayetanensis; Entamoeba histolytica; Gierdia lamblia; Trichomonas vaginalis; Toxoplasma gondii; Stenotrophomonas maitophilia; Burkhoideria cepacia; Burkholderia mallei* and *Burkhoideria pseudomailei; Franciseiia tularensis;* Gardnere!!a (e.g. *Gardneralia vaginalis* and *Gardnerαila mobiiuncus*); *Streptobaciiius moniliformis*; Fiavobacteriaceae, such as *Capnocytophaga* (e.g. *Capnocyiophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*); *Bartonella {Bartonella bacilliformis, Bartonella clarridgeiae, Bartonella elizabeihae, Bartonella henselae, Bartonella quintana* and *Bartonella vinsonii arupensis*); *Leptospira* (e.g. *Leptospira bifiexa, Leptospira borgpetersenii, Leptospira inadai, Leptospira interrogans, Leptospira kirschneri, Leptospira noguchii, Leptospira santarosai* and *Leptospira weiiii*); Spiri!lium (e.g. *Spirillum minus*)] Baceteroides (e.g. *Bacteroides caccae, Bacteroides capiiiosus, Bacteroides coaguians, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides spianchinicus, Bacteroides stercoris, Bacteroides tectus, Bacteroides thetaiotaomicron, Bacteroides uniformis, Bacteroides ureoiyticus* and *Bacteroides vuigatus*); *Prevotella* (e.g. *Prevoteiia bivia, Prevotella buccae, Prevoteiia corporis, Prevoteiia dentalis {Mstsuokella dentalis), Prevotella denticola, Prevoteiia disiens, Prevotella enoeca, Prevotella heparinoiytica, Prevotella intermedia, Prevoteiia loeschii, Prevotella meianinogenica, Prevoteiia nigrescens, Prevotella oralis, Prevoteiia oris, Prevotella ouiora, Prevotella tannerae, Prevotella venoralis* and *Prevoteiia zoogieoformans*); *Porpbyromonas* (e.g. *Porphyromonas asaccharoiytica, Porphyromonas cangingivalis, Porphyromonas canoris, Porphyromonas cansuici, Porphyromonas catoniae, Porphyromonas circumdentaria, Porphyromonas crevioricanis, Porphyromonas endodontalis, Porphyromonas*

*gingivalis, Porphyromonas gingivicanis, Porphyromonas ievii* and *Porphyromonas macacae*); *Fusobacterlum* (e.g. *F. gonadiaformans, F. mortiferum, F. naviforme, F. necrogenes, F. necrophorum necrophorum, F. necrophorum fundiliforme, F. nucleatum nucieatum, F. nucleatum fusiforme, F. nucleatum polymorphum, F. nucleatum vincentii, F. periodontium, F. russii, F. uicerans* and *F. varium*); *Chlamydia* (e.g. *Chlamydia trachomatis*); *Cryptosporidium* (e.g. *C. parvum, C. hominis, C. canis, C. fells, C. meleagridis* and *C. muris*); *Chlamydophila* (e.g. *Chiamydophiia abortus* {*Chlamydia psittaci*), *Chlamydophila pneumoniae* {*Chlamydia pneumoniae*) and *Chlamydophila psittaci* {*Chlamydia psittaci*)); *Leuconostoc* (e.g. *Leuconostoc citreum, Leuconostoc cremoris, Leuconosioc dextranicum, Leuconostoc iactis, Leuconostoc mesenteroides* and *Leuconostoc pseudomesenteroides*); *Gemeiia* (e.g. *Gemeiia bergeri, Gemeiia haemoiysans, Gemeiia morbiiiorum* and *Gemeiia sanguinis*); and *Ureapiasma* (e.g. *Ureaplasma parvum* and *Ureapiasma ureaiyticum*).

An infection may also refer to the presence of more than one type of bacteria, in or on a subject. For example, the bacterial infection may be caused by a mixture of Gram-positive bacteria, by a mixture of Gram-negative bacteria or by a mixture of both Gram-positive and Gram-negative bacteria. An infection may also be caused, for example, by a mixture of aerobic bacteria, anaerobic bacteria or both.

In use, in one example, a hydrogel is formed with a bioactive self-assembling peptide.

The term "hydrogel" as used herein refers to a polymeric material that exhibits the ability to swell in a liquid and retain a significant portion of liquid within its structure without dissolution. In some examples, the liquid is a pharmaceutically acceptable solvent, such as water or phosphate buffered saline, which should not interfere with the biological activity of the bioactive self-assembling peptide.

In one example, the hydrogel comprises the bioactive self-assembling peptide as described herein. In another example, the hydrogel comprises a bioactive self-assembling peptide as described herein and a self-assembling peptide.

In some examples, the hydrogel comprises about 20 to about 100% (w/v) of the bioactive self-assembling peptide.

In one example, the hydrogel comprises about 20% w/w (RADA)$_4$-GG-(PAMP-12) (SEQ ID NO: 2). In one example, the hydrogel comprises more than 20% w/w (RADA)$_4$-GG-(PAMP-12) (SEQ ID NO: 2).

In a specific example, the bioactive self-assembling peptide is (RADA)4-GG-PAMP12 (SEQ ID NO: 2), and the self-assembling peptide is (RADA)4 (SEQ ID NO: 1). In one example, the hydrogel comprises about 20% w/w (RADA)$_4$-GG-(PAMP-12) (SEQ ID NO: 2). In one example, the hydrogel comprises more than 20% w/w (RADA)$_4$-GG-(PAMP-12) (SEQ ID NO: 2).

In some examples, the self-assembling peptides, nanofibers, and hydrogels, are pharmaceutically acceptable.

The term pharmaceutically acceptable refers to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The hydrogel is administered to a subject for the treatment of a bacterial infection.

The hydrogel may be administered alone or in combination with other treatments, either simultaneously or sequentially, dependent upon the condition to be treated.

In treating a subject, a therapeutically effective amount of a bioactive self-assembling peptide may be administered to the subject.

The term "therapeutically effective amount" or "effective amount" is an amount sufficient to effect beneficial or desired clinical results. An effective amount can be administered in one or more administrations.

The compounds and compositions may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot/for example, subcutaneously or intramuscularly.

In some examples, the bioactive-self assembling peptide may be lyophilized.

In some examples, the bioactive-self assembling peptide may be formulated for presentation in unit-dose or multi-dose containers, for example sealed ampoules and vials, and may be stored in lyophilized condition. In some examples, extemporaneous injection solutions and suspensions may be prepared from sterile powders, granules and tablets.

In some examples, a lyophilized bioactive-self assembling peptide may be incorporated in to a bandage, and/or dressing, and/or, or other application device.

The term "bandage" and "dressing" are used to refer to a piece of material that is in direct contact with a wound, and may be used to promote healing and/or prevent further harm. Bandages are available in a wide range of types, from generic cloth strips, to specialized shaped bandages designed for a specific limb or part of the body, although bandages can often be improvised as the situation demands, using clothing, blankets or other material. Accordingly, bandages and dressing include, but are not limited to, wrappable lengths, patches, plasters, compresses.

In some examples, the bioactive self-assembling peptide, nanofibers, or hydrogels, disclosed herein may be used in the methods described herein in combination with standard treatment regimes, as would be known to the skilled worker.

For example, common drugs and/or combinations of such drugs used in the treatment of a bacterial infection include, but are not limited to, antimicrobial agents.

The term "antimicrobial agent" as used herein refers to any entity with antimicrobial activity. In some examples, the antimicrobial agent inhibits or reduces the growth and/or kills a microbe, such as bacteria.

An antimicrobial agent can be, for example, but not limited to, a small molecule, a peptide, a peptidomimetic, an antibody or a fragment thereof, a nucleic acid, an enzyme, an aptamer, Examples of classes of antibiotics include, but are not limited to, β-lactams, including the penicillins, cephalosporins monobactams, methicillin, and carbapenems; aminoglycosides, e.g., gentamicin, kanamycin, neomycin, tobramycin, netilmycin, paromomycin, and amikacin; tetracyclines, e.g., doxycycline, minocycline, oxytetracycline, tetracycline, and demeclocycline; sulfonamides (e.g., mafenide, sulfacetamide, sulfadiazine and sulfasalazine) and trimethoprim; quinolones, e.g., ciprofloxacin, norfloxacin, and ofloxacin; glycopeptides (e.g., vancomycin, telavancin, teicoplanin); macrolides, which include for example, erythromycin, azithromycin, and clarithromycin; carbapenems (e.g., ertapenem, doripenem, meropenem, and imipenem); cephalosporins (e.g., cefadroxil, cefepime, and ceftobiprole); lincosamides (e.g., clindamycin, and lincomycin); monobactams (e.g., aztreonam); nitrofurans (e.g., furazolidone, and nitrofurantoin); (13) Penicillins (e.g., amoxicillin, and Penicillin G); polypeptides (e.g., bacitracin, colistin, and polymyxin B); and other antibiotics, e.g., ansamycins, polymycins, carbacephem, chloramphenicol, lipopeptide, and drugs against mycobacteria (e.g., the ones causing diseases in mammals, including tuberculosis (*Mycobacterium tuberculosis*) and leprosy (*Mycobacterium leprae*), and any combinations thereof.

Method of the invention are conveniently practiced by providing the compounds and/or compositions used in such method in the form of a kit. Such kit preferably contains the composition. Such a kit preferably contains instructions for the use thereof.

To gain a better understanding of the invention described herein, the following examples are set forth. It should be understood that these examples are for illustrative purposes only. Therefore, they should not limit the scope of this invention in anyway.

EXAMPLES

Traditionally, mast cells are best known for their important role in allergic inflammatory responses, however, mast cells also participate in protective actions such as wound healing, angiogenesis and host defense against pathogens and animal venoms [1-5]. Mature mast cells are distributed widely in connective tissues that interface with the external environment throughout the body: skin, digestive tract, mucosa of lung and airways, etc. [6, 7]. These cells contain a number of secretory granules, which are filled with a large amount of pre-formed and pre-activated compounds like histamine, heparin and serine proteases, cytokines and growth factors [1, 8]. Upon stimulation, mast cell degranulation occurs and leads to the rapid release of pre-stored and neo-synthesized mediators. Therefore, mast cells can be considered as the first responders that play a critical role in both host defense and tissue repair.

Many mediators produced by mast cells have direct anti-microbial activity. Anti-microbial peptides expressed by mammalian mast cells, known as cathelicidins, play a key role in innate immune defense against invasive bacterial infection [9]. Some studies have indicated the potential applications of harnessing mast cell mediated host defense for bacterial infections. For example, the cathelicidin peptide LL-37 released from mast cells during degranulation have a potent antimicrobial effect against the multidrug-resistant bacteria *Enterococcus faecalis* [10], and provide protection against necrotic skin infection caused by Group A *Streptococcus* [11].

Mast cells produce a large variety of pro-angiogenic factors, including prestored and de novo expressed vascular endothelial growth factor (VEGF) upon activation. It was reported that low dose irradiation increases VEGF production by mast cells and promotes vascular regeneration in an ischemic model [12]. Additionally, mast cells release pre-formed fibroblast growth factor (FGF)-2 from their secretory granules upon stimulation, which promote angiogenesis during chronic inflammation [13]. The intraperitoneal injection of stimulus compound 48/80 causes a vigorous angiogenic response in rat and mice tissue [14, 15]. In addition, mast cell proteases, tryptase and chymase, are directly involved in angiogenesis [16, 17].

Wound healing is a dynamic process that involves in inflammation, tissue regeneration and remodeling, and mast cell play an important role in it. During skin wound healing, mast cells can interact with macrophages, endothelial cells, and fibroblasts, and promote tissue granulation, cell migration, angiogenesis, and collagen maturation through the releasing of interleukin-4 (IL-4), VEGF, bFGF, chymase, and typtase, etc., into the local microenvironment [18-25]. It has been reported that anti-microbial peptides, LL-37, β-defensin 3, retrocyclin and protegrin activate mast cell was described as a therapeutic potential in wound healing [26-28]. Recently, similar result has been described in a mice diabetes model that substance P stimulation improves skin wound healing in wild-type, but not mast cell deficient mice, implying the mast cells is required for proper wound healing and the therapeutic potential of manipulation of mast cell activation at certain site [21]. Another example of phototherapy is that using light-emitting diodes (LEDs) with 830 nm light to initiate dermal mast cell degranulation, which accelerate wound healing process with a controlled inflammatory process and benefit skin rejuvenation [29].

Recently, scaffolds that interact with the immune system and trigger an immune response in damaged tissue have been shown to be an exciting emerging therapeutic avenue for promoting tissue repair [30-33]. As described, mast cells wildly populate connective tissues such as skin and these cells can rapidly release large amounts of pre-formed granule compounds upon appropriate stimulation. Therefore, being able to specifically activate the immune response of mast cells in a localized manner so as to directly affect wound healing, angiogenesis and a beneficial host defense is a new therapeutic strategy. Classically, mast cells are activated via an antigen-induced IgE (FcE-RI) receptor cross-linking on the cell membrane, however, human mast cells can also respond to a series of cationic peptides, including substance P [34-36], vasoactive intestinal peptide (VIP) [35], cortistatin-14 [34-36], LL-37 [37], β-defensins [38] and PAMP-12 [34], etc., through a non-selective cell-membrane receptor, Mas-related G-protein coupled receptor member X2 (MRGPRX2. or MrgX2).

PAMP-12 (Ac-FRKKWNKWALSR-CONH2) (SEQ ID NO: 3), or PAMP [9-20] is the C-terminal region of proadrenomedullin N-terminal 20 peptide (PAMP-20, or PAMP [1-20]), a 20-amino acid hypotensive peptide expressed in the adrenal medulla. PAMP-12 (SEQ ID NO: 3) was identified as an endogenous ligand for MRGPRX2, which induced the activation of mast cells in a dose-dependent manner [34]. This work has shown that the extent of mast cell activation can be controlled by the concentration of bioactive peptides within the tissue. Compared to systemic administration, the localized administration of bioactive peptides at the site of interest can result in reduced side-effects, a greater therapeutic outcome, while using a lower overall amount of peptide drug.

Self-assembling peptide based materials are becoming recognized as a robust platform for many tissue engineering applications. They are of particular interest given they are composed of peptides that can be cleared by the host, do not come from animal sources, and allow for the direct implementation of bioactive moieties to induce a variety of therapeutic functions. The ion-complementary self-assembling peptide, (RADA)4 (SEQ ID NO: 1), is comprised of alternating hydrophobic and hydrophilic amino acids and has been shown to form well-ordered β-sheet nanofibers that subsequently develop into a highly hydrated (>99.5% water), 3-D hydrogel matrix in physiological solutions [39-46]. One advantage of (RADA)4 nanoscaffolds is the potential for molecular level programmability; biofunctionality of the assembled nanomatrix can be introduced by directly extending the self-assembling peptide sequence with bioactive motifs (e.g. cell adhesion,[47] angiogenesis,[48-50] bone regeneration,[51, 52] nerve regeneration,[53, 54] etc.).

In this work, the dose dependent effect PAMP-12 modified (RADA)4 (SEQ ID NO: 1) matrix on mast cell degranulation was studied. The activation of mast cells was found to be controllable through varying the amount of PAMP-12 tethered to the nanofiber matrix. Furthermore, through tethering of the PAMP-12 to the self-assembling matrix it was found that only mast cells in direct contact with the matrix were activated; illustrating that cell activation could be controlled locally.

Materials and Methods

Materials

Figure 1C:
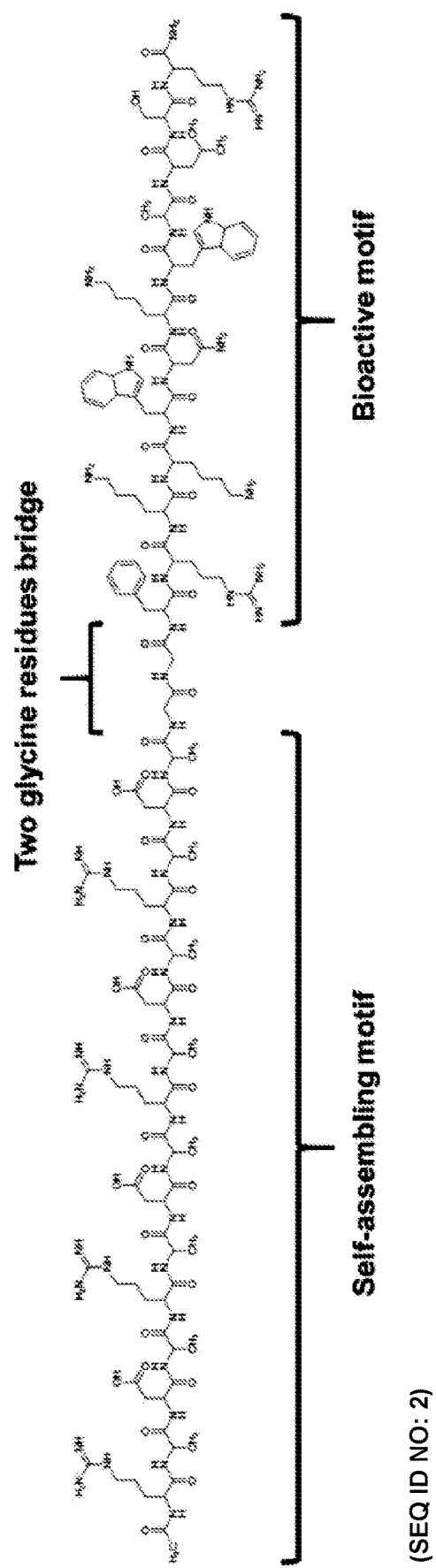

The PAMP-12 (SEQ ID NO: 3), (RADA)$_4$ (SEQ ID NO: 1) and (RADA)$_4$-GG-(PAMP-12) (SEQ ID NO: 2) peptide (95% purity) was purchased from RS Synthesis (Louisville, Ky., USA), checked for purity using mass spectroscopy and used without further purification. Endotoxin levels of all peptides were tested using ToxinSensor™Chromogenic LAL Endotoxin Assay Kit from GenScript (Piscataway, N.J., USA). (RADA)$_4$ (SEQ ID NO: 1) and (RADA)$_4$-GG-(PAMP-12) (SEQ ID NO: 2) contained <0.1 EU/mg endotoxin (e.q. 50 µl of 0.5% w/v nanoscaffold contain <0.05 EU endotoxin), and the endotoxin levels of PAMP-12 at working concentrations were less than 0.1 EU/ml. (Sensitivity: 0.005 EU/ml, $R^2$=0.9952). The 0.2 µm Anopore® Membrane Nunc Culture Inserts were purchased from Nalge Nunc International (Rochester, N.Y., USA). The chemical structures of (RADA)$_4$ (SEQ ID NO: 1) and (RADA)$_4$-GG-(PAMP-12) (SEQ ID NO: 2) are shown in FIG. 1A-C.

Hydrogel Matrices Preparation (RADA)$_4$ (SEQ ID NO: 1) and (RADA)$_4$-GG-(PAMP-12) (SEQ ID NO:2) stock solutions (1.0% w/v) were prepared by dissolving peptide powder in syringe filtered (0.2 µm) Milli-Q water. Peptide stock solutions were sonicated for 30 min to avoid bulk aggregates and reduce viscosity. (RADA)$_4$ peptide solutions with different proportion of (RADA)$_4$-GG-(PAMP-12) (SEQ ID NO: 2) (0, 2.5, 5, 10, 20, 40, 80, 100% w/w) were mixed with 1x PBS (pH 7.4) at a ratio of 1:1 (v/v) to get hydrogel matrices with peptide concentration of 0.5% w/v. Fifty µl of the mixture was placed at the bottom of a 96-well plate or well insert, overnight at 4° C. and washed with HEPES buffer (10 mM, with 0.4% BSA, pH 7.4) or PBS for 3 times.

Atomic Force Microscopy (AFM)

The morphology of the hydrogel matrices were measured using Dimension 3100 Nanoman Atomic Force Microscopy (AFM, Veeco Metrology, LLC) with tapping mode, tip radius of 8 nm. Matrix solutions used in AFM studies were prepared by 500 times diluted with Mili-Q water. A drop (5 ul) of each solution was placed on freshly cleaved mica substrate then rise with water. The surfaces were air dried overnight at room temperature before being imaged.

Cell Culture

LAD2 (Laboratory of Allergic Diseases 2) human mast cells were incubated in StemPro-34 SFM medium (Life Technologies, Rockville, Md.) supplemented with 2 mM L-glutamine, 100 I/ml penicillin, 50 µg/ml streptomycin, 100 ng/ml recombinant human SCF (Peprotech, Rocky Hill, N.J.). Cells were maintained at 0.1×10$^6$ cells/ml at 37° C. and 5% $CO_2$. Cell suspensions were isolated via centrifugation (200 g, 5 min, at room temperature) and media was replaced every 3-7 days.

Evaluation of Degranulation Using the β-Hexosaminidase (β-Hex) Release Assay

For each well, 0.25×10$_5$ LAD2 cells were washed and resuspended in 90 µl HEPES buffer (10 mM, with 0.4% BSA, pH 7.4), and activated by adding 10 µl peptide solutions (PAMP-12 (SEQ ID NO: 2), (RADA)$_4$ (SEQ ID NO: 1) and (RADA)$_4$-GG-(PAMP-12) (SEQ ID NO: 2)) in PBS (1×, pH 7.4) for 30 min at 37° C., the final concentrations of peptide are 0, 0.01, 0.1, 1, 10, 20, 50, 100 µM respectively. β-hex release was quantified through analysis of the hydrolysis of p-nitrophenyl N-acetyl-b-D-glucosamide (Sigma Aldrich, Oakville, ON, Canada) in 0.1 M sodium citrate buffer (pH 4.5) for both the supernatant and in total cell lysates solubilized with 0.01% Triton X-100 for 90 min at 37° C. The reaction was stopped by adding glycine buffer (pH 10.7). Read absorbance at 405 nm with reference filter at 620 nm. The percent-age of β-hex released into the supernatant was calculated by the β-hex contents of supernatant and cell lysate.

To evaluate the effect of the matrices on degranulation, 0.25×10$^5$ LAD2 cells in 50 µl HEPES buffer (10 mM, with 0.4% BSA, pH 7.4) were carefully placed on the top of 50 µl hydrogel matrices, and the β-hex release was measured as described. After 30 min incubation, cell free supernatant and total cells with the matrices were collected by centrifugation (300 g, 5 min) for analysis.

To evaluate the immobilization effect of (RADA)$_4$-GG-(PAMP-12) (SEQ ID NO: 2) in the matrices. As shown in FIG. 6 (A), 0.25×105 LAD2 cells in 100 µl HEPES buffer (10 mM, with 0.4% BSA, pH 7.4) were co-incubated with well inserts that contain 50 µl of self-assembling matrix (20% and 100% w/w of (RADA)$_4$-GG-(PAMP-12) (SEQ ID NO: 2)) or PAMP-12 (SEQ ID NO: 3) solution in HEPES buffer (10 mM, with 0.4% BSA, pH 7.4) with the corresponding concentration (0.29 and 1.46 mM respectively). After 30 min incubation, inserts were removed, and the β-hex release was measured as described.

Cell Viability Analysis Using XTT Assay

LAD2 cells were suspended in culture medium (50 µl, 1.0×10$^6$ cells/ml) and placed on top of 50 µl of hydrogel matrix or culture medium solution. After an 4 h or 24 h incubation, cell viability was measured using a 2,3-bis-(2-methoxy-4-nitro-5-sulfophenyl)-2H-tetrazolium-5-carboxanilide (XTT) proliferation kit (Roche Molecular Biochemicals, Indianapolis, Ind., USA), according to the manufacturer's supplied instructions. To facilitate a uniform distribution of color throughout the hydrogel matrix, 50 µl of DMSO was added into each well prior to analysis.

Laser-Scanning Confocal Microscopy

For each sample, 0.25×105 LAD2 cells in 50 µl culture medium were allowed to incubate with 50 µl hydrogel matrix for 30 min at 37° C. After incubation, the medium was disposed, and hydrogel matrix was carefully washed by warm PBS for 3 times to remove non-adherent cells. Hydrogel matrices were then fixed in 3.7% paraformaldehyde in PBS for 20 min at room temperature and 3 times washed in PBS. Cells were permeabilized with 0.1% Triton X-100 in PBS for 5 min, washed in PBS for 3 times, then followed by 3% BSA blocking for 30 min and 3 times washing in PBS. To stain F-actin, samples were incubated with 0.5 µM Phalloidin-FITC (Sigma-Aldrich, USA) for 30 minutes and followed by 3 times washing in PBS. Cell nuclei were stained with 1 ug/mL DAPI (Sigma-Aldrich, USA) in PBS for 30 min. After 3 times washing in PBS, Z-slice images of the matrix with adhered LAD2 cells were collected using Laser Scanning Confocal Microscopy (LSM710, Carl Zeizz AG, Oberkochen, Germany) with an inverted 10× objective.

Harvesting of Human Skin Tissue

Human skin was harvested from abdominoplasty surgical discard specimens obtained following written informed consent as approved by the University of Alberta research ethics board. All tissue was from healthy non-smokers in their 30s.

Fluorescent Staining of Mast Cells in Human Skin

Human skin biopsies were fixed in 10% formalin for at least 24 h, embedded in paraffin and mounted on glass slides were incubated at 60° C. for 20 min before deparaffinization and rehydration in two changes of xylene and five changes of ethanol in descending concentrations [55]. Sections then underwent heat mediated antigen retrieval in sodium citrate buffer, pH 6.0 in a conventional pressure cooker for approximately 10 min, or just prior to boiling and cooled for 20 min. Image-iT™ RX Signal Enhancer (Thermo Fisher Scientific Inc, Waltham, Mass.) was used for 30 min to enhance signal and mask autofluorescence, followed by 1 h incubation with 10% goat serum. After washing 3 times for 5 min in PBS, sections were incubated with a 1:500 dilution of an anti-mast cell tryptase primary antibody (ab134932 Abcam, Cambridge, UK) for 16 h at 4° C. then washed again. Subsequently slides were incubated with a 1:350 dilution of Alexa Fluor® 546 goat anti-rabbit secondary antibody (Thermo Fisher Scientific Inc, Waltham, Mass.) for 1.5 h. Washing and mounting of sections with ProLong® Gold Antifade with DAPI (Thermo Fisher Scientific Inc, Waltham, Mass.) was then performed prior to image analysis. Sections were photographed using NIS Elements Imaging Software on a Nikon Eclipse Ti-E inverted microscope.

In Vitro Activation of Mast Cells in Human Skin

Human skin was separated from the underlying adipose tissue using a 15 blade scalpel. The epidermis was then removed using a Padgett dermatome (Integra LifeSciences Corporation, Cincinnati, Ohio) set to 0.25 mm thickness. The deepithelialized dermis was then divided into multiple pieces 1 $cm^2$ using sharp surgical scissors. Control or active hydrogel matrix (100 µl) was then layered onto the exposed surface of the dermis. Pieces were then placed with the gel side up in 6 well plates (Corning) with 2 ml of Dulbecco's Modified Eagle Medium (Life) per well, and incubated for 2 h in a cell culture incubator with 5% $CO_2$, 95% humidity at 37° C. For some groups, PBS and PAMP-12 PBS solution were used as negative and positive control. Following this, tissue pieces were removed and snap frozen in liquid nitrogen and stored at −80° C. until further processing.

Droplet Digital PCR (ddPCR) for Mast Cell Tryptase Gene (TPSAB1) Expression

Total RNA was isolated from tissue by placing pieces individually into a high frequency pulverizer which was kept cool with liquid nitrogen, and shaken until all tissue was ground into a fine powder. This powder was then dissolved in Trizol (Life), and mRNA extracted using the manufacturer's standard protocol. cDNA was generated using a reverse transcription kit (Qiagen) using the manufacturer's standard protocol. To obtain the absolute quantity of TPSAB1 transcripts, ddPCR (QX100, Bio-Rad, Hercules, Calif.) was employed using 5 ng of each cDNA sample and ddPCR supermix for the specific probes (Bio-Rad) according to manufacturer's protocols. The PrimeTime qPCR assays for TPSAB1 (Assay ID, Hs. PT.58.19121290.g), CMA1 (Assay ID, Hs. PT.58.27270145.g) and a reference gene, ACTB (Assay ID, Hs. PT.39a.22214847) were obtained from IDT (Coralville, Iowa). The ddPCR conditions comprised of an initial denaturation for 10 min at 95° C. followed by 45 cycles of denaturation for 30 s at 94° C., and annealing and extension for 1 min at 60° C., and the final extension for 10 min at 98° C. Template cDNA was omitted from the ddPCR reaction for no template control (NTC). QuantaSoft Software (Bio-Rad) was employed to analyze ddPCR results, and the absolute concentration of TPSAB1 transcripts in each sample determined by ddPCR was divided by the ACTB transcripts and presented as percentage based on normal skin samples (NS average taken as 100).

Statistical Analysis

All data were conducted in at least quadruplicate with independent repeats and presented as average ±standard error of the mean (SEM). The statistical significance of differences between mean values was determined using one-way ANOVA followed by two-tailed Student's t-test for analysis of variance, where significance was evaluated for $p<0.05$, $p<0.01$, $p<0.001$.

Results

Figure 3:
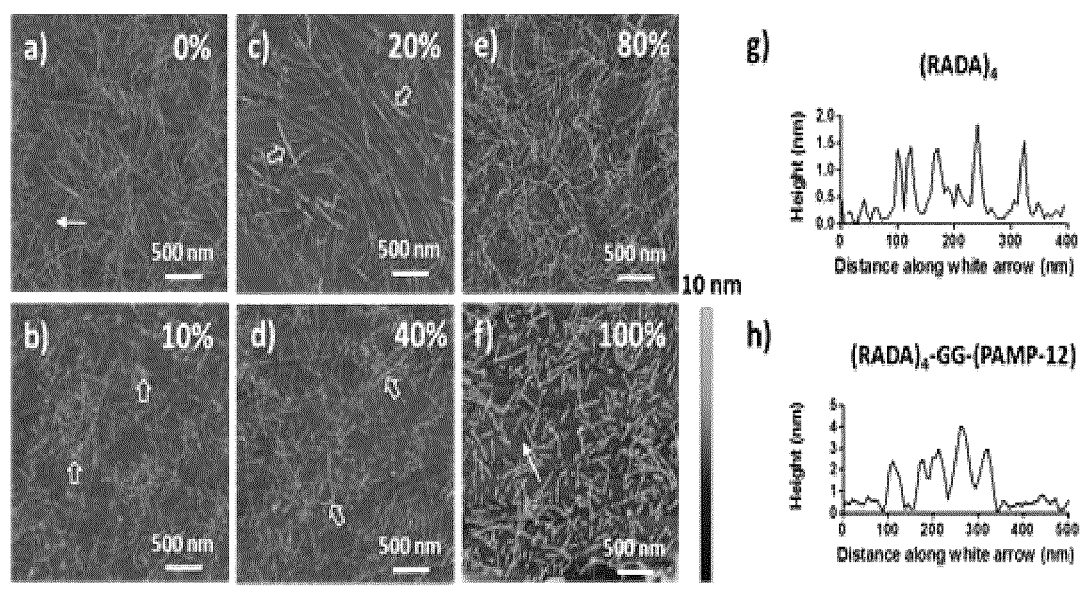
FIG. 3 the morphology of 0.5% w/v self-assembling peptide matrix measured by AFM. The ratio of $(RADA)_4$-GG-(PAMP-12) (SEQ ID NO: 2): $(RADA)_4$ (SEQ ID NO: 1) was: a) 0:100; b) 10:90; c) 20:80; d) 40:60; e) 80:20; f) 100:0, g) the height of $(RADA)_4$ nanofiber, h) the height of $(RADA)_4$-GG-(PAMP-12) nanofiber. The sections were followed with the white arrow shown in a) and f). The examples of thicker sections of the nanofiber in b), c) and d) were highlighted by red arrows.

In order to evaluate the self-assembly property of $(RADA)_4$-GG-(PAMP-12) (SEQ ID NO: 2) peptide, AFM characterization of the $(RADA)_4$ (SEQ ID NO: 1) matrices with different ratios of $(RADA)4$-GG-(PAMP-12) (SEQ ID NO: 2): $(RADA)_4$ (SEQ ID NO: 1) was conducted. AFM results for nanofiber matrices are summarized in FIG. 3 (a-f). Pure 0.5% w/v $(RADA)_4$ (SEQ ID NO: 1) produced the expected long, evenly distributed, nanofibers (FIG. 3a). Upon incorporation of 10% w/w $(RADA)_4$-GG-(PAMP-12) (SEQ ID NO: 2) (FIG. 3b), the nanofiber network overall maintained a similar structure as the $(RADA)_4$ control. However, thick sections were observed within the formed nanofibers that may indicate the presence of the PAMP-12 sequence within the formed nanofibers (see arrow). As the $(RADA)_4$-GG-(PAMP-12) (SEQ ID NO: 2) proportion increased to 20% and 40% w/w, longer segments of increased thickness appeared embedded in the nanofibers. Although, shorter nanofibers that less than 200 nm were observed, most of the nanofibers in 20% and 40% w/w are longer than 500 nm. When the proportion of $(RADA)_4$-GG-(PAMP-12) (SEQ ID NO: 2) reach 80% w/w, an evenly distributed nanofiber network was observed (FIG. 3e). Those nanofibers were significantly thicker than pure $(RADA)_4$ nanofibers. The nanostructure formed by pure $(RADA)_4$-GG-(PAMP-12) (SEQ ID NO: 2) (FIG. 3f) showed thick and short nanofibers and even small nanoparticles. Most of the nanofibers were less than 500 nm, and the nanoparticles were smaller than 200 nm. It is possible that the observed nanoparticle-structures may actually be nanofiber fragments.

AFM cross section heights for pure $(RADA)_4$ (SEQ ID NO: 1) and $(RADA)_4$-GG-(PAMP-12) (SEQ ID NO: 2) samples were collected and illustrated in FIGS. 3g and h. Each peak could be directly correlated to structures that were crossed by the diagonal white arrows in FIGS. 3a and f. The cross-sectional profile of pure $(RADA)_4$ (SEQ ID NO: 1) samples (FIG. 3g) show nanofiber heights of ~1.5 nm, which can be considered as single nanofiber. However, the profile for nanofibers formed from pure $(RADA)_4$-GG-(PAMP-12) (SEQ ID NO: 2) showed dramatic increase in height to 2.5-3.5 nm, which is much larger than the height of $(RADA)4$ nanofiber. The difference in cross sectional height for each peptide formed nanofiber can help us to understand the morphology change among matrices with different proportion of peptides.

Effect of (RADA)4-GG-(PAMP-12) (SEQ ID NO: 2) on Mast Cell Degranulation

Figure 4:
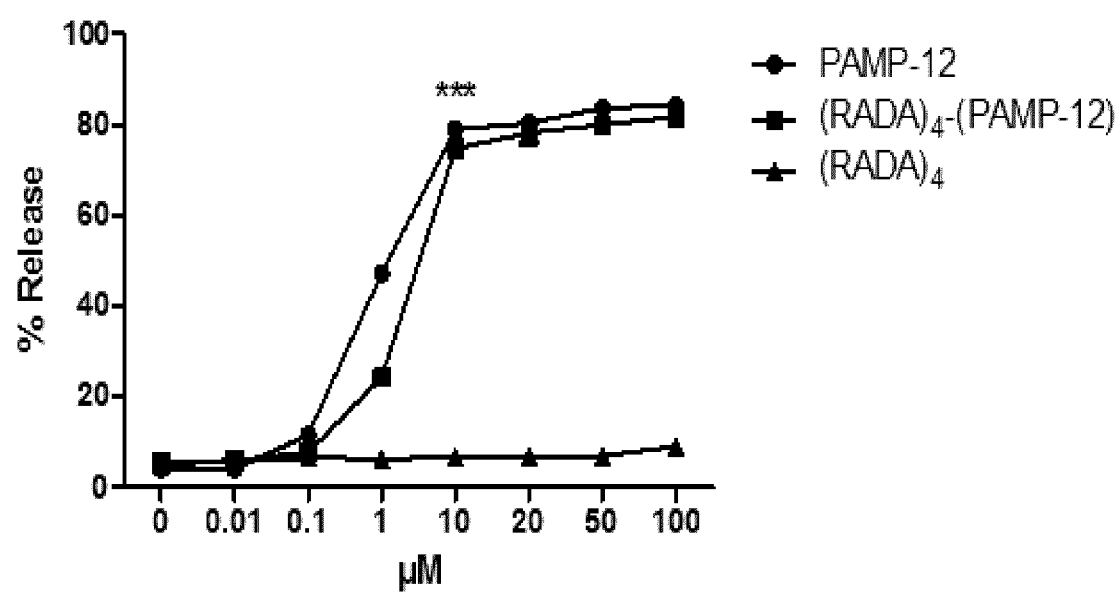
FIG. 4 The optimal response of LAD2 cells to PAMP-12, $(RADA)_4$ (SEQ ID NO: 1), and $(RADA)_4$-GG-(PAMP-12) (SEQ ID NO: 2) on mast cell degranulation. LAD2 cells were activated with peptides for 30 min and β-hex release was measured. Data represent mean±1 SEM, for n≥3 repeats.

To ascertain if PAMP-12 activity was retained upon tethering to the RADA moiety, PAMP-12 (SEQ ID NO: 3), (RADA)$_4$ (SEQ ID NO: 1) and (RADA)$_4$-GG-(PAMP-12) (SEQ ID NO: 2) were evaluated to see if they induced human mast cell degranulation using the β-hex release assay. LAD2 cells were stimulated with various concentrations of each peptide. It was observed that (RADA)$_4$ was not capable of initiating the degranulation of LAD2 cells, however, the peptide stimulus PAMP-12 (SEQ ID NO: 3) and the functionalized (RADA)$_4$-GG-(PAMP-12) (SEQ ID NO: 2) induced significant degranulation (e.g. p<0.001 at 10 µM) compared with PBS and (RADA)$_4$ solutions in a dose dependent manner. Furthermore, it was observed that the solution free PAMP-12 (SEQ ID NO: 3) and (RADA)$_4$-GG-(PAMP-12) (SEQ ID NO: 2) share a similar potency, plateauing at ~75% β-hex release for a concentration of 10 µM (FIG. 4). Based upon this, 10 µM of PAMP-12 was chosen as the positive control for further studies.

Hydrogel Matrices with (RADA)$_4$-GG-(PAMP-12) Induce Mast Cell Degranulation in a Dose Dependent Manner The PAMP-12 modified nanofiber matrix was able to cause LAD2 degranulation in a concentration dependent manner. Similar to the previous result in FIG. 4, the matrix composed of pure (RADA)$_4$ (SEQ ID NO: 1) did not induce degranulation and showed no significant difference compared to the negative control (PBS) (p>0.05). The degranulation activity increased proportionally with the increase in (RADA)$_4$-GG-(PAMP-12) (SEQ ID NO: 2) from 2.5 to 20% w/w, and the degranulation activity at 20% and 40% w/w of (RADA)$_4$-(PAMP-12) (64.2±3.4% and 70.2±7.1%, respectively) are statistically similar (p>0.05).

Hydrogel Matrix with 20% w/w of (RADA)$_4$-GG-(PAMP-12) Induce Mast Cell Degranulation Locally.

Figure 6A:
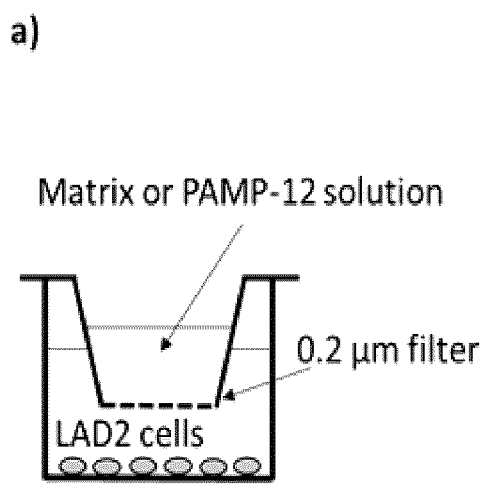
FIG. 6 Hydrogel matrix with 20% w/w of (RADA)4-GG-(PAMP-12) (SEQ ID NO: 2) induce mast cell degranulation locally. A). Schematic diagram of co-culture by well insert with 0.2 μm pore size filter. B). The effect of co-cultured PAMP-12 or hydrogel matrices on LAD2 degranulation. Data represent mean±1 SEM, for n≥3 repeats.
Figure 6B:
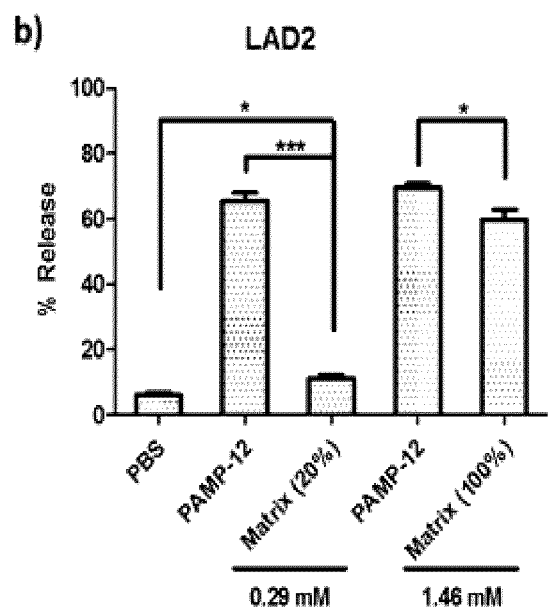

As shown in FIG. 6B, the 0.5% w/v matrix with 20% w/w of (RADA)$_4$-GG-(PAMP-12) (SEQ ID NO: 2) in insert induced very limited degranulation of LAD2 (11.1±1.1%), compared with incubating with 0.29 mM PAMP-12 (SEQ ID NO: 3) in insert (65.4±2.6%). The matrix of 100% w/w (RADA)$_4$-GG-(PAMP-12) (SEQ ID NO: 2) induced an obvious degranulation (59.6±3.1%), however, the activity is still significantly lower than incubating with 1.46 mM PAMP-12 in insert (69.5±1.2%) (p<0.05).

The Activation and Adhesion of LAD2 Cells on the Surface of Hydrogel Matrix

LAD2 interactions with the nanofiber matrices were characterized using confocal imaging (Z-slices) and 3D reconstruction using IMARIS 8 software (FIGS. 7a and b). Only a very small number of cells were found to be associated, post-wash, with the pure (RADA)$_4$ matrix after 30 min incubation (FIG. 7a). However, matrices containing 20% w/w (RADA)$_4$-GG-(PAMP-12) showed a considerable amount of cells retained after washing (FIG. 7b). For both systems, mast cells seemed to be found within the same plane, likely on the surface of the matrix.

Figure 7:
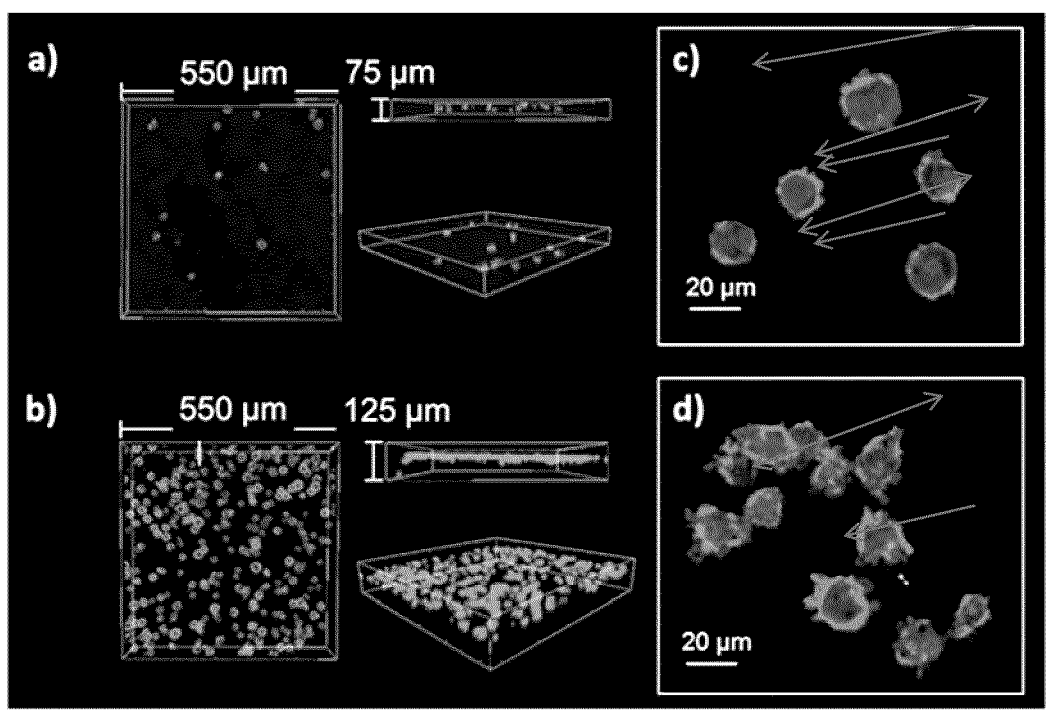
FIG. 7 Laser confocal scanning microscopy image of LAD2 cells and 0.5% w/v nanfiber matrices. F-actin (green—some examples shown with leader line with single arrow) and nuclei (blue—some examples shown with leader line with double arrows). (a, c) with pure $(RADA)_4$ (SEQ ID NO: 1); (b, d) with 20% w/w of $(RADA)_4$-GG-(PAMP-12) (SEQ ID NO: 2). (a, b) 3D distribution of cells in contact with hydrogel matrices. The Z-dimension scale was determined by the first and the last visible cell nuclei; (c, d) 2D images of cell morphology and F-actin organization.

Cytoskeleton reorganization is pivotal for cell morphology changes, adhesion, migration and exocytosis of mast cells during activation [58]. The effect of (RADA)$_4$-GG-(PAMP-12) (SEQ ID NO: 2) stimulation on actin cytoskeletal organization of these mast cells was further characterized using 2D imaging (FIG. 7 c and d). In mast cells stimulated by (RADA)$_4$-GG-(PAMP-12) (SEQ ID NO: 2), lamellipodia and filopodia were observed in association with the F-actin assemblies at and near the membrane features of the cell periphery (FIG. 7d). However, the F-action organization of LAD2 cells on pure (RADA)4 matrix are only observed to be ring shaped, with no obvious lamellipodia and filopodia structures (FIG. 7c). This data seems to suggest that cells retained on the PAMP-12 modified matrix are adhered and not been activated.

Cell Viability

Figure 8:
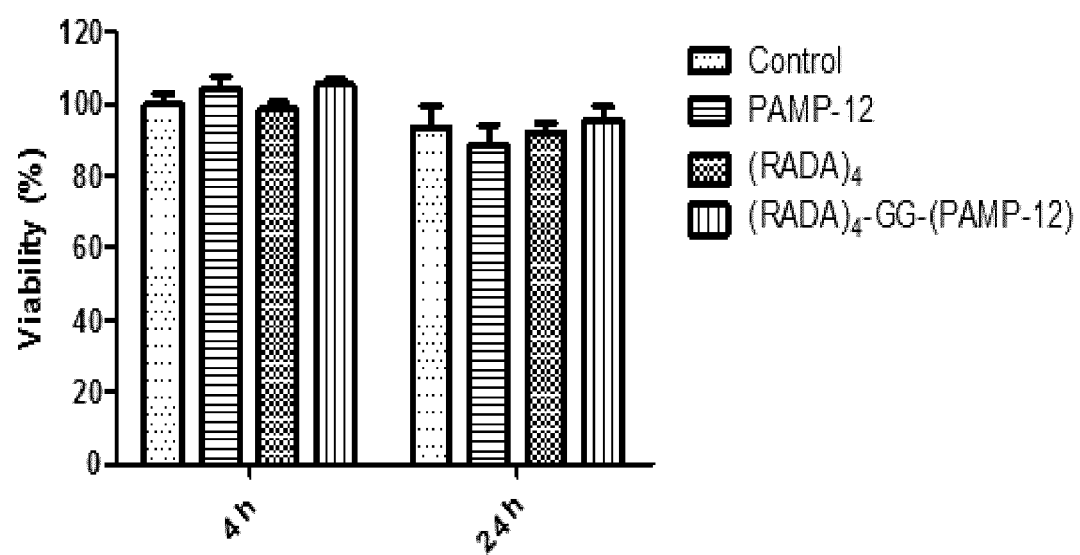
FIG. 8 Effect of hydrogel matrix on mast cell viability as determined using XTT assay, where cell viability of control at 4 his 100%. Data represent mean±1 SEM, for n≥3 repeats.

The effect of the hydrogel matrices on mast cell viability was evaluated using a standard XTT viability assay (FIG. 8). LAD2 cells (0.5×106 cells/ml) were incubated in PBS (Control), PAMP-12 (SEQ ID NO: 3) (10 µM), 0.5% w/v hydrogel matrices (pure (RADA)$_4$ (SEQ ID NO: 1) or with 20% w/w (RADA)$_4$-GG-(PAMP-12) (SEQ ID NO: 2)) for 4 h or 24 h. Results indicate that the PAMP-12 and hydrogel matrices was not cytotoxic to LAD2 cells and had no statistically significant effect on LAD2 proliferation after 24 h incubation.

The Distribution and Activation of Mast Cells in Human Skin Tissue

The distribution of mast cell in human skin tissue was observed by using immunofluorescent staining (FIG. 9a). Tryptase is the most abundant mast cell-specific serine proteinase contained in mast cells granules and has been used as a marker for mast cell activation. [59-61]. Mast cell identification and distribution in fixed tissue has been commonly determined using anti-typtase monoclonal antibody based immunohistochemistry [62, 63]. As shown in FIG. 9a, the tryptase (red) containing mast cells are clearly present and distributed evenly in human skin tissue.

The mRNA expression of TPSAB1 (tryptase) was used as an indicator of human mast cell activation [64-66]. There is a significant difference (p<0.05) of TPSAB1 expression between normal skin (NS) and normal skin without epidermis (NSE) as illustrated in FIG. 9b. After 4 h treatment with PAMP-12 (SEQ ID NO: 3), the TPSAB1 expression level was significantly increased (p<0.001) compared with untreated NSE. There was no significant different between (RADA)$_4$ hydrogel matrix treatment and untreated NSE, however, (RADA)$_4$-GG-(PAMP-12) hydrogel matrix successfully increased the TPSAB1 expression level (p<0.05). Again, it was observed that solution free NSE/PAMP-12 (224.2±9.920) and NSE/(RADA)$_4$-GG-(PAMP-12) (191.1±12.0) were not significantly different, despite the slight difference in average amounts (FIG. 9b).

DISCUSSION

In this study, we investigated the strategy of using the well-known peptide activator of mast cells, PAMP-12, conjugated to a self-assembling peptide matrix so as to determine if it was possible to manipulate the human innate immune response.

AFM techniques were used to verify the morphologies of matrices of pure and mixtures of (RADA)$_4$ (SEQ ID NO: 1) and (RADA)$_4$-GG-(PAMP-12) (SEQ ID NO: 2) and showed that nanofiber formation still occurred upon addition of the PAMP-12 (SEQ ID NO: 3) sequence. Pure (RADA)$_4$ (SEQ ID NO: 1) peptide nanofiber presents the expected thin and long nanofibers (FIGS. 3a and g), while pure (RADA)$_4$-GG-(PAMP-12) (SEQ ID NO: 2) peptide formed thick and short nanofibers (FIGS. 3f and h). It was also observed that the nanofibers formed from mixtures consisted of thick (RADA)$_4$-GG-(PAMP-12) (SEQ ID NO: 2) and thin (RADA)$_4$ segments, when (RADA)$_4$-GG-(PAMP-12) (SEQ ID NO: 2) proportion increased, the continuous thick pieces appeared (FIG. 3a-f). This is likely due to the longer sequence of (RADA)$_4$-GG-(PAMP-12) (SEQ ID NO: 2) increasing the fiber diameter. Due to the electrostatic attraction between the various nanofiber constructs and the mica used in AFM studies, it is expected that the lack of any other type of structures means that that these peptides are incorporating into the resultant nanofibers only.

Figure 5:
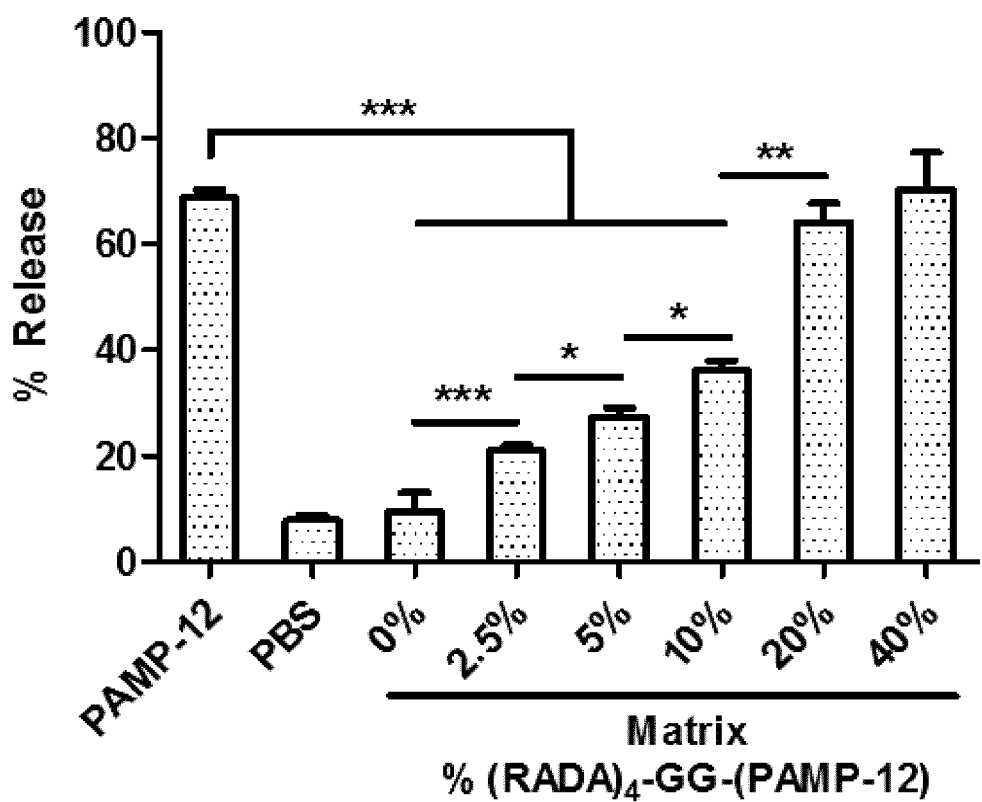
FIG. 5 The effect of self-assembling hydrogel matrices with different ration of $(RADA)_4$-GG-(PAMP-12) (SEQ ID NO: 2) on LAD2 degranulation. Data represent mean±1 SEM, for n≥3 repeats.

It has been demonstrated that (RADA)4-GG-(PAMP-12) (SEQ ID NO: 2) induced mast cell degranulation in a dose dependent manner, the potency of which was similar to solution free PAMP-12 peptides (FIG. 4). The self-assembling peptide (RADA)$_4$, by contrast, did not activate human mast cell degranulation, suggesting that the degranulation activity of (RADA)$_4$-GG-(PAMP-12) was fully attributed to the bioactive PAMP-12 domain. Pure (RADA)4 matrix was unable to induce LAD2 degranulation, while matrices with (RADA)$_4$-GG-(PAMP-12) induced mast cell activation significantly, which was proportional to the percent composition of (RADA)$_4$-GG-(PAMP-12) (SEQ ID NO: 2). Where the 0.5% w/v matrix with 20% w/w of (RADA)$_4$-GG-(PAMP-12) (SEQ ID NO: 2) was able to cause the most degranulation of human mast cell (FIG. 5).

Cell culture inserts used in FIG. 6 have a porous membrane at the bottom of the insert that separates the two compartments, while allowing for diffusion of molecules smaller than the pore size between compartments. In order to evaluate the immobility of (RADA)$_4$-GG-(PAMP-12) in matrix, we loaded the 0.5% w/v (RADA)$_4$-GG-(PAMP-12) matrix (20% and 100% w/w) and relative concentration of PAMP-12 solution (0.29 and 1.46 mM) in the 96 well inserts (pore size: 0.2 µm, namely 200 nm), and then incubated with LAD2 cells for 30 min for the degranulation assay (FIG. 6a). The effect of the porous membrane is negligible on the diffusion of molecules from the insert to the cell culture medium as both the 0.5% w/v (RADA)4 nanofiber matrix has a smaller pore size range (5-200 nm) compared to the membrane (200 nm) [56, 57]. Culture results shown in FIG. 6b indicate that the soluble (RADA)$_4$-GG-(PAMP-12) peptides in 20% w/w of (RADA)4-GG-(PAMP-12) matrix only slightly induced mast cell degranulation compared with PBS control. This is likely due to the fact that all the PAMP-12 sequences were immobilized within the nanofiber matrix and prevented from diffusing through the porous barrier. The control of PAMP-12 solution (0.29 mM) in the insert significantly induced mast cell degranulation, which is due to the diffusion of small size PAMP-12 into mast cell environment. In contrast, pure (RADA)$_4$-GG-(PAMP-12) matrix (100% w/w) degranulation percentage was significantly lower than the PAMP-12 control (1.46 mM) (p<0.05), but was still considerable. This is likely due to the fact that, as shown with the AFM results (FIG. 3c), nanofibers formed using 100% (RADA)$_4$-GG-(PAMP-12) yielded a large proportion of peptide nanofibers shorter than 200 nm (FIG. 3f), thus, those short nanofibers consist of (RADA)$_4$-GG-(PAMP-12) may diffuse through the membrane, and lead to a great degranulation of mast cell. Whereas, AFM result (FIG. 3c) show that nanofibers doped with with 20% w/w of (RADA)$_4$-GG-(PAMP-12) mainly consist of long nanofibers, and thus the vast majority of PAMP-12 is tethered to the nanofibers and cannot enter the cell culture compartment directly.

Figure 2:
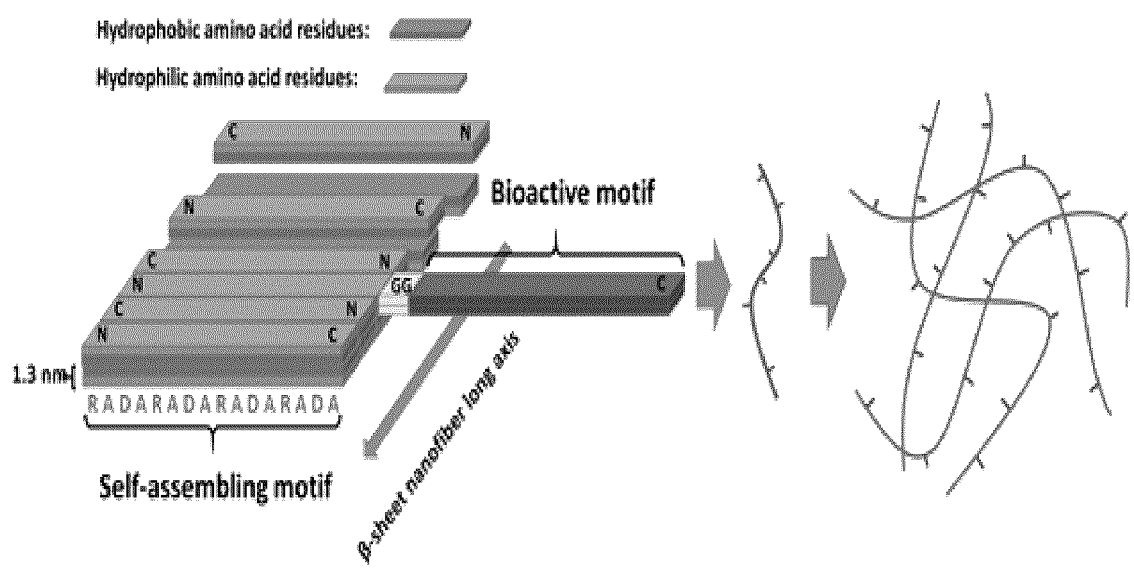
FIG. 2 depicts the schematic of the hydrogel matrix with both $(RADA)_4$ (SEQ ID NO: 1) and $(RADA)_4$-GG-(PAMP-12) (SEQ ID NO: 2) self-assembling peptides.

The interaction between LAD2 cells and the nanofiber matrices after 30 min incubation is summarized in FIG. 7 a and b. Apparently, cell adhesion to the (RADA)$_4$ matrix was not favoured as most of the LAD2 cells were washed away (FIG. 7a). This may due to the lack of cell binding site on (RADA)$_4$ nanofiber. However, the surface of hydrogel matrix with 20% w/w of (RADA)4-GG-(PAMP-12) (SEQ ID NO: 2) was covered with a large number of cells (FIG. 7b). Obviously the PAMP-12 motif provided a binding domain for these cells on formed nanofibers (FIG. 2). Also the mast cell activation may enhance the adhesion progress as the activation may contribute to mast cell adhesion to nature ECM proteins [70-75]. The LAD2 cells activation by (RADA)$_4$-GG-(PAMP-12) (SEQ ID NO: 2) can be identified by the 2D imaging (FIG. 7d), and cell morphology that included the presence of lamellipodia and filopodia were observed via the structures of F-actin assemblies. This similar result was observed for actin rearrangement during secretagogues (e.g., poly-L-lysine) mediated mast cell activation in previous work [76]. However, the adhered LAD2 cells on pure (RADA)$_4$ matrix have no obvious lamellipodia and filopodia structures, and presented as typical F-actin rings only (FIG. 7c) confirming a lack of activation. The observation of FIG. 7c and dcoincides with the reported F-actin organization of resting and activated mast cells [58], and correspond to the results of degranulation test that (RADA)$_4$ has no effect on mast cell activation but (RADA)$_4$-GG-(PAMP-12) (SEQ ID NO: 2) initiate the activation process (FIGS. 4 and 5). The interaction between mast cells and artificial ECM is rarely reported. Self-assembling peptides, including (RADA)4 (SEQ ID NO: 1) have also been used as nanoscaffold for 3D cell culture [56]. Thus, mast cells are not sensitive to (RADA)$_4$ indicate that (RADA)4 matrix could be amenable as a matrix for mast cell 3D culture. This is important because immature mast cells are recruited through the circulation and become mature in connective tissues [77], however, currently, most of the mast cell studies are in suspension.

To investigate the effect of designed hydrogel matrix on mast cells in human skin tissue, the TPSAB1 (tryptase) was used as an indicator of mast cell activation. The quantification of TPSAB1 mRNA levels in human tissue is a convenient method to determine the degree of mast cell activation [64-66]. As the TPSAB1 expression need more than 30 min, the cell viability and proliferation for these times needed to be measured. XTT assay results indicated that both matrices and stimulation has no significant effect on LAD2 cell viability after 24 h (FIG. 8). We also demonstrated that mast cells were distribute evenly in human skin tissue, which was identified by staining preformed tryptase in mast cell granules (FIG. 9a). As shown in FIG. 9b, after 4 h incubation, the gene expression levels between NS and NSE groups have a significant different (p<0.05), this may due to different mast cell distribution in the epidermis, or the mast cell activation during epidermis removing process. The expression levels of NSE/PAMP-12 and NSE/(RADA)$_4$-GG-(PAMP-12) groups increased significantly (p<0.001 and p<0.01, respectively) compared with NSE group, which indicated the activation of human skin mast cell. Moreover, NSE/(RADA)4 has no effect on TPSAB1 expression, which corresponded to previous in vitro degranulation tests using LAD2 cells (FIGS. 4 and 5) and confocal imaging results (FIG. 7).

CONCLUSION

We developed self-assembling bioactive peptide, (RADA)$_4$-GG-(PAMP-12) (SEQ ID NO: 2), which could activate human mast cells in a dose-dependent manner. The (RADA)$_4$-GG-(PAMP-12) (SEQ ID NO: 2) peptide can self-assembled with (RADA)$_4$ peptide to form nanofiber matrices with controlled amounts of PAMP-12 modification. The degree of mast cell activation can be manipulated through adjusting the bioactive peptide ratio in the matrix and the bioactive peptide can be anchored in the in situ forming nanofiber matrix, which may benefit the localized stimulation and minimize the potential side effects. The designed hydrogel matrix can successfully activate tissue-resident mast cells in human skin by contact.

REFERENCES

[1] S. Wernersson, G. Pejler, Mast cell secretory granules: armed for battle, Nat. Rev. Immunol. 14(7) (2014) 478-494.
[2] C. Noli, A. Miolo, The mast cell in wound healing, Veterinary dermatology 12(6) (2001) 303-313.
[3] K. Norrby, Mast cells and angiogenesis, APMIS 110(5) (2002) 355-371.
[4] F. Féger, S. Varadaradjalou, Z. Gao, S. N. Abraham, M. Arock, The role of mast cells in host defense and their subversion by bacterial pathogens, Trends Immunol. 23(3) (2002) 151-158.
[5] J. H. Kim, Y. Jung, B.-S. Kim, S. H. Kim, Stem cell recruitment and angiogenesis of neuropeptide substance P coupled with self-assembling peptide nanofiber in a mouse hind limb ischemia model, Biomaterials 34(6) (2013) 1657-1668.
[6] Y. Kitamura, Heterogeneity of mast cells and phenotypic change between subpopulations, Annu. Rev. Immunol. 7(1) (1989) 59-76.
[7] S. J. Galli, S. Nakae, M. Tsai, Mast cells in the development of adaptive immune responses, Nat. Immunol. 6(2) (2005) 135-142.
[8] A. Grützkau, S. Krüger-Krasagakes, H. Baumeister, C. Schwarz, H. Kögel, P. Welker, U. Lippert, B. M. Henz, A. Möller, Synthesis, storage, and release of vascular endothelial growth factor/vascular permeability factor (VEGF/VPF) by human mast cells: implications for the biological significance of VEGF206, Mol. Biol. Cell 9(4) (1998) 875-884.
[9] M. Zanetti, Cathelicidins, multifunctional peptides of the innate immunity, J. Leukoc. Biol. 75(1) (2004) 39-48.
[10] M. Scheb-Wetzel, M. Rohde, A. Bravo, O. Goldmann, New insights into the antimicrobial effect of mast cells against *Enterococcus faecalis*, Infect. Immun. 82(11) (2014) 4496-4507.
[11] V. Nizet, T. Ohtake, X. Lauth, J. Trowbridge, J. Rudisill, R. A. Dorschner, V. Pestonjamasp, J. Piraino, K. Huttner, R. L. Gallo, Innate antimicrobial peptide protects the skin from invasive bacterial infection, Nature 414(6862) (2001) 454-457.
[12] B. Heissig, S. Rafii, H. Akiyama, Y. Ohki, Y. Sato, T. Rafael, Z. Zhu, D. J. Hicklin, K. Okumura, H. Ogawa, Low-dose irradiation promotes tissue revascularization through VEGF release from mast cells and MMP-9-mediated progenitor cell mobilization, The Journal of experimental medicine 202(6) (2005) 739-750.
[13] Z. Qu, J. M. Liebler, M. R. Powers, T. Galey, P. Ahmadi, X.-N. Huang, J. C. Ansel, J. H. Butterfield, S. R. Planck, J. T. Rosenbaum, Mast cells are a major source of basic fibroblast growth factor in chronic inflammation and cutaneous hemangioma, The American journal of pathology 147(3) (1995) 564.
[14] K. Norrby, A. Jakobsson, J. Sörbo, Mast-cell-mediated angiogenesis: a novel experimental model using the rat mesentery, Virchows Archiv B 52(1) (1986) 195-206.
[15] K. Norrby, A. Jakobsson, J. Sörbo, Mast-cell secretion and angiogenesis, a quantitative study in rats and mice, Virchows Archiv B 57(1) (1989) 251-256.
[16] D. Ribatti, G. Ranieri, Tryptase, a novel angiogenic factor stored in mast cell granules, Exp. Cell Res. 332(2) (2015) 157-162.
[17] M. Muramatsu, J. Katada, M. Hattori, I. Hayashi, M. Majima, Chymase mediates mast cell-induced angiogenesis in hamster sponge granulomas, Eur. J. Pharmacol. 402(1) (2000) 181-191.
[18] A. Trautmann, G. Krohne, E.-B. Bröcker, C. E. Klein, Human mast cells augment fibroblast proliferation by heterotypic cell-cell adhesion and action of IL-4, The Journal of Immunology 160(10) (1998) 5053-5057.
[19] Z. Qu, X. Huang, P. Ahmadi, P. Stenberg, J. M. Liebler, A.-C. Le, S. R. Planck, J. T. Rosenbaum, Synthesis of Basic Fibroblast Growth Factor by Murine Mast Cells-Regulation by Transforming Growth Factor Beta, Tumor Necrosis Factor Alpha, and Stem Cell Factor, Int. Arch. Allergy Appl. Immunol. 115(1) (1997) 47-54.
[20] M. Artuc, B. Hermes, U. Stckelings, A. Grützkau, B. Henz, Mast cells and their mediators in cutaneous wound healing—active participants or innocent bystanders?, Exp. Dermatol. 8(1) (1999) 1-16.
[21] A. Tellechea, E. C. Leal, A. Kafanas, M. E. Auster, S. Kuchibhotla, Y. Ostrovsky, F. Tecilazich, D. Baltzis, Y. Zheng, E. Carvalho, Mast Cells Regulate Wound Healing in Diabetes, Diabetes (2016) db150340.
[22] N. Shiota, Y. Nishikori, E. Kakizoe, K. Shimoura, T. Niibayashi, C. Shimbori, T. Tanaka, H. Okunishi, Pathophysiological role of skin mast cells in wound healing after scald injury: study with mast cell-deficient W/Wv mice, Int. Arch. Allergy Appl. Immunol. 151(1) (2009) 80-88.
[23] B. C. Wulff, T. A. Wilgus, Mast cell activity in the healing wound: more than meets the eye?, Exp. Dermatol. 22(8) (2013) 507-510.
[24] J. Gailit, M. J. Marchese, R. R. Kew, B. L. Gruber, The differentiation and function of myofibroblasts is regulated by mast cell mediators, J. Invest. Dermatol. 117(5) (2001) 1113-1119.
[25] J. Douaiher, J. Succar, L. Lancerotto, M. F. Gurish, D. P. Orgill, M. J. Hamilton, S. A. Krilis, R. L. Stevens, Development of mast cells and importance of their tryptase and chymase serine proteases in inflammation and wound healing, Adv. Immunol. 122 (2014) 211.
[26] T. Hirsch, M. Spielmann, B. Zuhaili, M. Fossum, M. Metzig, T. Koehler, H. U. Steinau, F. Yao, A. B. Onderdonk, L. Steinstraesser, Human beta-defensin-3 promotes wound healing in infected diabetic wounds, The journal of gene medicine 11(3) (2009) 220-228.
[27] A. J. Duplantier, M. L. Van Hoek, The human cathelicidin antimicrobial peptide LL-37 as a potential treatment for polymicrobial infected wounds, Frontiers in immunology 4 (2013) 143.
[28] K. Gupta, A. Kotian, H. Subramanian, H. Daniell, H. Ali, Activation of human mast cells by retrocyclin and protegrin highlight their immunomodulatory and antimicrobial properties, Oncotarget 6(30) (2015) 28573.
[29] R. G. Calderhead, J. Kubota, M. A. Trelles, T. Ohshiro, One mechanism behind LED phototherapy for wound healing and skin rejuvenation: key role of the mast cell, Laser Ther. 17(3) (2008) 141-148.
[30] K. Sadtler, A. Singh, M. T. Wolf, X. Wang, D. M. Pardoll, J. H. Elisseeff, Design, clinical translation and immunological response of biomaterials in regenerative medicine, Nature Reviews Materials 1 (2016) 16040.
[31] K. Sadtler, K. Estrellas, B. W. Allen, M. T. Wolf, H. Fan, A. J. Tam, C. H. Patel, B. S. Luber, H. Wang, K. R. Wagner, Developing a pro-regenerative biomaterial scaffold microenvironment requires T helper 2 cells, Science 352(6283) (2016) 366-370.

[32] S. F. Badylak, A scaffold immune microenvironment, Science 352(6283) (2016) 298-298.

[33] Y. Vigneswaran, H. Han, R. De Loera, Y. Wen, X. Zhang, T. Sun, C. Mora-Solano, J. H. Collier, Peptide biomaterials raising adaptive immune responses in wound healing contexts, Journal of Biomedical Materials Research Part A (2016).

[34] B. D. McNeil, P. Pundir, S. Meeker, L. Han, B. J. Undem, M. Kulka, X. Dong, Identification of a mast-cell-specific receptor crucial for pseudo-allergic drug reactions, Nature 519(7542) (2015) 237-241.

[35] K. Tatemoto, Y. Nozaki, R. Tsuda, S. Konno, K. Tomura, M. Furuno, H. Ogasawara, K. Edamura, H. Takagi, H. Iwamura, Immunoglobulin E-independent activation of mast cell is mediated by Mrg receptors, Biochem. Biophys. Res. Commun. 349(4) (2006) 1322-1328.

[36] N. Robas, E. Mead, M. Fidock, MrgX2 is a high potency cortistatin receptor expressed in dorsal root ganglion, J. Biol. Chem. 278(45) (2003) 44400-44404.

[37] H. Subramanian, K. Gupta, Q. Guo, R. Price, H. Ali, Mas-related Gene X2 (MrgX2) Is a Novel G Protein-coupled Receptor for the Antimicrobial Peptide LL-37 in Human Mast Cells RESISTANCE TO RECEPTOR PHOSPHORYLATION, DESENSITIZATION, AND INTERNALIZATION, J. Biol. Chem. 286(52) (2011) 44739-44749.

[38] H. Subramanian, K. Gupta, D. Lee, A. K. Bayir, H. Ahn, H. Ali, β-Defensins activate human mast cells via Mas-related gene X2, The Journal of Immunology 191(1) (2013) 345-352.

[39] H. Yokoi, T. Kinoshita, S. G. Zhang, Dynamic reassembly of peptide RADA16 nanofiber scaffold, P Natl Acad Sci USA 102(24) (2005) 8414-8419.

[40] S. G. Zhang, F. Gelain, X. J. Zhao, Designer self-assembling peptide nanofiber scaffolds for 3D tissue cell cultures, Semin Cancer Biol 15(5) (2005) 413-420.

[41] S. G. Zhang, Fabrication of novel biomaterials through molecular self-assembly, Nat Biotechnol 21(10) (2003) 1171-1178.

[42] F. Gelain, L. D. Unsworth, S. Zhang, Slow and sustained release of active cytokines from self-assembling peptide scaffolds, J. Control. Release 145(3) (2010) 231-239.

[43] S. Koutsopoulos, L. D. Unsworth, Y. Nagai, S. Zhang, Controlled release of functional proteins through designer self-assembling peptide nanofiber hydrogel scaffold, Proceedings of the National Academy of Sciences 106(12) (2009) 4623-4628.

[44] Y. Nagai, L. D. Unsworth, S. Koutsopoulos, S. Zhang, Slow release of molecules in self-assembling peptide nanofiber scaffold, J. Control. Release 115(1) (2006) 18-25.

[45] M. Kabiri, I. Bushnak, M. T. McDermot, L. D. Unsworth, Toward a mechanistic understanding of ionic self-complementary peptide self-assembly: role of water molecules and ions, Biomacromolecules 14(11) (2013) 3943-3950.

[46] A. Saini, K. Koss, L. D. Unsworth, Effect of Peptide Concentration on Water Structure, Morphology, and Thermal Stability of Self-Assembling (RADA) 4 Peptide Matrices, Journal of Biomaterials and Tissue Engineering 4(11) (2014) 895-905.

[47] S. G. Zhang, Emerging biological materials through molecular self-assembly, Biotechnol Adv 20(5-6) (2002) 321-339.

[48] X. M. Wang, A. Horii, S. G. Zhang, Designer functionalized self-assembling peptide nanofiber scaffolds for growth, migration, and tubulogenesis of human umbilical vein endothelial cells, Soft Matter 4(12) (2008) 2388-2395.

[49] X. Liu, X. M. Wang, A. Horii, X. J. Wang, L. Qiao, S. G. Zhang, F. Z. Cui, In vivo studies on angiogenic activity of two designer self-assembling peptide scaffold hydrogels in the chicken embryo chorioallantoic membrane, Nanoscale 4(8) (2012) 2720-2727.

[50] J. H. Kim, Y. Jung, B. S. Kim, S. H. Kim, Stem cell recruitment and angiogenesis of neuropeptide substance P coupled with self-assembling peptide nanofiber in a mouse hind limb ischemia model, Biomaterials 34(6) (2013) 1657-1668.

[51] H. T. Pan, S. F. Hao, Q. X. Zheng, J. F. Li, J. Zheng, Z. L. Hu, S. H. Yang, X. D. Guo, Q. Yang, Bone induction by biomimetic PLGA copolymer loaded with a novel synthetic RADA16-P24 peptide in vivo, Mat Sci Eng C-Mater 33(6) (2013) 3336-3345.

[52] A. Horii, X. M. Wang, F. Gelain, S. G. Zhang, Biological Designer Self-Assembling Peptide Nanofiber Scaffolds Significantly Enhance Osteoblast Proliferation, Differentiation and 3-D Migration, Plos One 2(2) (2007).

[53] Z. W. Zou, Q. X. Zheng, Y. C. Wu, X. D. Guo, S. H. Yang, J. F. Li, H. T. Pan, Biocompatibility and bioactivity of designer self-assembling nanofiber scaffold containing FGL motif for rat dorsal root ganglion neurons, J Biomed Mater Res A 95A(4) (2010) 1125-1131.

[54] Z. W. Zou, T. Liu, J. F. Li, P. D. Li, Q. Ding, G. Peng, Q. X. Zheng, X. L. Zeng, Y. C. Wu, X. D. Guo, Biocompatibility of functionalized designer self-assembling nanofiber scaffolds containing FRM motif for neural stem cells, J Biomed Mater Res A 102(5) (2014) 1286-1293.

[55] J. Wang, J. Ding, H. Jiao, D. Honardoust, M. Momtazi, H. A. Shankowsky, E. E. Tredget, Human hypertrophic scar-like nude mouse model: Characterization of the molecular and cellular biology of the scar process, Wound Repair Regen. 19(2) (2011) 274-285.

[56] F. Gelain, A. Horii, S. G. Zhang, Designer self-assembling peptide scaffolds for 3-D tissue cell cultures and regenerative medicine, Macromolecular Bioscience 7(5) (2007) 544-551.

[57] C. A. Hauser, S. Zhang, Designer self-assembling peptide nanofiber biological materials, Chem. Soc. Rev. 39(8) (2010) 2780-2790.

[58] P. Dráber, V. Sulimenko, E. Dráberová, Cytoskeleton in mast cell signaling, Deciphering new molecular mechanisms of mast cell activation (2014) 34.

[59] I. T. Harvima, N. M. Schechter, R. J. Harvima, J. E. Fraki, Human skin tryptase: purification, partial characterization and comparison with human lung tryptase, Biochimica et Biophysica Acta (BBA)-Protein Structure and Molecular Enzymology 957(1) (1988) 71-80.

[60] L. B. Schwartz, D. D. Metcalfe, J. S. Miller, H. Earl, T. Sullivan, Tryptase levels as an indicator of mast-cell activation in systemic anaphylaxis and mastocytosis, N. Engl. J. Med. 316(26) (1987) 1622-1626.

[61] S. I. Butrus, K. I. Ochsner, M. B. Abelson, L. B. Schwartz, The level of tryptase in human tears: an indicator of activation of conjunctival mast cells, Ophthalmology 97(12) (1990) 1678-1683.

[62] A. F. Walls, D. B. Jones, J. H. Williams, M. K. Church, S. T. Holgate, Immunohistochemical identification of mast cells in formaldehyde-fixed tissue using monoclonal antibodies specific for tryptase, The Journal of pathology 162(2) (1990) 119-126.

[63] L. W. HUNT, T. V. Colby, D. A. WEILER, S. SUR, J. H. Butterfield, Immunofluorescent staining for mast cells in idiopathic pulmonary fibrosis: quantification and evidence for extracellular release of mast cell tryptase, Mayo Clin. Proc., Elsevier, 1992, pp. 941-948.

[64] A. L. Christy, M. E. Walker, M. J. Hessner, M. A. Brown, Mast cell activation and neutrophil recruitment promotes early and robust inflammation in the meninges in EAE, J. Autoimmun. 42 (2013) 50-61.

[65] K. S. H. Blatman, N. Gonsalves, I. Hirano, P. J. Bryce, Expression of mast cell-associated genes is upregulated in adult eosinophilic esophagitis and responds to steroid or dietary therapy, The Journal of allergy and clinical immunology 127(5) (2011) 1307.

[66] C. V. Velasquez, A. D. Roman, N. T. P. Lan, N. T. Huy, E. S. Mercado, F. E. Espino, M. L. M. Perez, V. T. Q. Huong, T. T. Thuy, V. D. Tham, Alpha tryptase allele of Tryptase 1 (TPSAB1) gene associated with Dengue Hemorrhagic Fever (DHF) and Dengue Shock Syndrome (DSS) in Vietnam and Philippines, Hum. Immunol. 76(5) (2015) 318-323.

[67] A. Schneider, J. A. Garlick, C. Egles, Self-assembling peptide nanofiber scaffolds accelerate wound healing, PLoS ONE 3(1) (2008) e1410.

[68] H. Meng, L. Chen, Z. Ye, S. Wang, X. Zhao, The effect of a self-assembling peptide nanofiber scaffold (peptide) when used as a wound dressing for the treatment of deep second degree burns in rats, Journal of Biomedical Materials Research Part B: Applied Biomaterials 89(2) (2009) 379-391.

[69] A. Saini, K. Serrano, K. Koss, L. D. Unsworth, Evaluation of the hemocompatibility and rapid hemostasis of (RADA) 4 peptide-based hydrogels, Acta Biomater. (2015).

[70] V. Lam, J. Kalesnikoff, C. W. Lee, V. Hernandez-Hansen, B. S. Wilson, J. M. Oliver, G. Krystal, IgE alone stimulates mast cell adhesion to fibronectin via pathways similar to those used by IgE+antigen but distinct from those used by Steel factor, Blood 102(4) (2003) 1405-1413.

[71] H. Vliagoftis, Thrombin induces mast cell adhesion to fibronectin: evidence for involvement of protease-activated receptor-1, The Journal of immunology 169(8) (2002) 4551-4558.

[72] A. Rosbottom, C. L. Scudamore, H. von der Mark, E. M. Thornton, S. H. Wright, H. R. Miller, TGF-β1 regulates adhesion of mucosal mast cell homologues to laminin-1 through expression of integrin α7, The Journal of Immunology 169(10) (2002) 5689-5695.

[73] J. Dastych, D. D. Metcalfe, Stem cell factor induces mast cell adhesion to fibronectin, The Journal of Immunology 152(1) (1994) 213-219.

[74] H. L. Thompson, P. D. Burbelo, D. D. Metcalfe, Regulation of adhesion of mouse bone marrow-derived mast cells to laminin, The Journal of Immunology 145 (10) (1990) 3425-3431.

[75] S. Kruger-Krasagakes, A. Grützkau, R. Baghramian, B. M. Henz, Interactions of immature human mast cells with extracellular matrix: expression of specific adhesion receptors and their role in cell binding to matrix proteins, J. Invest. Dermatol. 106(3) (1996) 538-543.

[76] Z. Deng, T. Zink, H.-y. Chen, D. Walters, F.-t. Liu, G.-y. Liu, Impact of actin rearrangement and degranulation on the membrane structure of primary mast cells: a combined atomic force and laser scanning confocal microscopy investigation, Biophys. J. 96(4) (2009) 1629-1639.

[77] M. F. Gurish, K. F. Austen, The diverse roles of mast cells, The Journal of experimental medicine 194(1) (2001) F1-F6.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A bioactive self-assembling peptide for activating mast cells, comprising: a first peptide comprising a self-assembling peptide that mediates self-assembly, and a second peptide comprising PAMP-12 (SEQ ID NO: 3).

2. The bioactive self-assembling peptide of claim 1, wherein said first peptide comprises the peptide (RADA)4 (SEQ ID NO: 1).

3. The bioactive self-assembling peptide of claim 2, further comprising a linker positioned between said first peptide and said second peptide, wherein said linker comprises the amino acid sequence Gly-Gly.

4. The bioactive self-assembling peptide of claim 1, comprising the peptide (RADA)4-GG-(PAMP-12) (SEQ ID NO: 2).

5. A hydrogel comprising a bioactive self-assembling peptide for activating mast cells, comprising: a first peptide comprising a self-assembling peptide that mediates self-assembly, and a second peptide comprising PAMP-12 (SEQ ID NO: 3).

6. The hydrogel of claim 5, wherein said first peptide comprises the peptide (RADA)4 (SEQ ID NO: 1).

7. The hydrogel of claim 6, further comprising a linker positioned between said first peptide and said second peptide, wherein said linker comprises the amino acid sequence Gly-Gly.

8. The hydrogel of claim 6, wherein said self-assembling peptide comprises the peptide (RADA)4 (SEQ ID NO: 1).

9. The hydrogel of claim 5, wherein the bioactive self-assembling peptide comprises the peptide (RADA)4-GG-(PAMP-12) (SEQ ID NO: 2).

10. The hydrogel of claim 5, comprising at least about 20% (w/w) of said bioactive self-assembling peptide.

11. The hydrogel of claim 10, wherein the bioactive self-assembling peptide comprises the peptide (RADA)4-GG-(PAMP-12) (SEQ ID NO: 2).

12. The hydrogel of claim 5, comprising between about 20% to 40% (w/w) of said bioactive self-assembling peptide.

13. A method of treating a wound in a subject, comprising: administering the hydrogel of claim 5, to a subject in need thereof.

14. The method of claim 13, further comprising administering an antibiotic to the subject.

15. The method of claim 13, wherein said subject is a human.

* * * * *